US 8,299,114 B2

(12) United States Patent
Dubois et al.

(10) Patent No.: US 8,299,114 B2
(45) Date of Patent: Oct. 30, 2012

(54) BICYCLIC DERIVATIVES OF AZABICYCLIC CARBOXAMIDES, PREPARATION THEREOF AND THERAPEUTIC USE THEREOF

(75) Inventors: Laurent Dubois, Paris (FR); Yannick Evanno, Paris (FR); Catherine Gille, Paris (FR); André Malanda, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 12/840,661

(22) Filed: Jul. 21, 2010

(65) Prior Publication Data

US 2011/0009400 A1 Jan. 13, 2011

Related U.S. Application Data

(63) Continuation of application No. PCT/FR2009/000051, filed on Jan. 20, 2009.

(30) Foreign Application Priority Data

Jan. 22, 2008 (FR) ..................................... 08 00309

(51) Int. Cl.
*A01N 43/38* (2006.01)
*A61K 31/405* (2006.01)
*A61K 31/40* (2006.01)
*C07D 209/04* (2006.01)
*C07D 209/42* (2006.01)
(52) U.S. Cl. ......... 514/415; 514/419; 548/469; 548/492
(58) Field of Classification Search .................. 548/469, 548/492; 514/415, 419
See application file for complete search history.

(56) References Cited

U.S. PATENT DOCUMENTS

| | | | | |
|---|---|---|---|---|
| 7,384,969 B2 * | 6/2008 | Dubois et al. | .................. | 514/414 |
| 7,407,950 B2 * | 8/2008 | Dubois et al. | ............ | 514/211.09 |
| 7,557,134 B2 * | 7/2009 | Dubois et al. | .................. | 514/414 |
| 7,582,671 B2 * | 9/2009 | Dubois et al. | .................. | 514/414 |
| 7,868,024 B2 * | 1/2011 | Dubois et al. | .................. | 514/339 |
| 2010/0222368 A1 * | 9/2010 | Dubois et al. | ............ | 514/255.05 |
| 2011/0009364 A1 * | 1/2011 | Dubois et al. | ................... | 514/63 |

FOREIGN PATENT DOCUMENTS

| WO | 2006024776 | * | 3/2006 |
|---|---|---|---|
| WO | WO2006/024776 A1 | | 3/2006 |
| WO | 2006072736 | * | 7/2006 |
| WO | WO2006/072735 A1 | | 7/2006 |
| WO | 2007010144 | * | 1/2007 |
| WO | WO2007/010144 A1 | | 1/2007 |
| WO | WO2007010138 | | 1/2007 |

OTHER PUBLICATIONS

West, Anthony R., Solid State Chemistry and its Applications, Wiley, New York, 1988, pp. 358 & 365.*
Babin, P.,"Synthese d'aryl-et heteroarylsilanes par scission de l'hexamethyldisilane," Journal of Organometallic Chemistry (1993), vol. 446, pp. 135-138.
Davies, Stephen G. et al., "Preparation of Tricarbonyl(n6-pyridine)chromiurn(0)Complexes," Journal of the Chemical Society, Perkin Transactions 1 (1991), pp. 501-507.
Shirakawa, Eiji et al., "Diphenylphosphinophenolate: a ligand for the palladium-catalysed silylation of aryl halides activating simultaneously both palladium and silicon," Chemical Communications (2000), pp. 1895-1896.
Matsumoto, Hideyuki et al., "Silicon-Carbon Bond Formation by the Reaction of Disilanes with Halobenzenes in the Presence of Tetrakis-(Triphenylphosphine)Palladium(0)," Journal of Organometallic Chemistry (1975), vol. 85, pp. C1-C3.
Hoesl, Cornelia E. et al., "Synthesis of Sterically Demanding 3-Silylpyridines and their use in Asymmetric Synthesis with Chrial N-Acyliminium Ions," Heterocycles (2002),vol. 58, pp. 383-392.
Meyers, A.I. et al., "The Displacement of Methoxy by Amino Groups in Aryloxazolines. A Novel Approach to o-Amino-, o-Alkylamino-, and o-Dialkylaminobenzoic Acids," Journal of Organic Chemistry (1977), vol. 42, pp. 2653-2654.
Ishimaru, Kaori et al., "Diastereoselective Synthesis of trans-N-Benzyl-2-(2-Methylphenyl)-6-Phenyl-4-Piperidone," Heterocycles (2001), vol. 55, No. 8, pp. 1591-1598.
Klapars, Artis et al., "A General and Efficient Copper Catalyst for the Amidation of Aryl Halides and the N-Arylation of Nitrogen Heterocycles," Journal of the American Chemical Society (2001), vol. 123, pp. 7727-7729.
Antilla, Jon C. et al., "The Copper-Catalyzed N-Arylation of Indoles," Journal of the American Chemical Society (2002), vol. 124, pp. 11684-11688.
Furstner, Alois et al., "Iron-Catalyzed Cross-Coupling Reactions," Journal of the American Chemical Society (2002), vol. 124, pp. 13856-13863.
Stokes, Benjamin J. et al., "Intramolecular C-H Amination Reactions: Exploitation of the Rh2(II)-Catalyzed Decomposition of Azidoacrylates," Journal of the American Chemical Society (2007), vol. 129, pp. 7500-7501.
Williams, Theresa M. et al., "5-Chloro-3-(phenylsulfonyl)indole-2-carboxamide: A Novel, Non-Nucleoside Inhibitor of HIV-1 Reverse Transcriptase," Journal of Medicinal Chemistry (1993), vol. 36, pp. 1291-1294.

(Continued)

*Primary Examiner* — Niloofar Rahmani
(74) *Attorney, Agent, or Firm* — Scully, Scott, Murphy & Presser, P.C.

(57) ABSTRACT

The disclosure relates to compounds of formula (I):

wherein $X_1$, $X_2$, $X_3$, $X_4$, Y, n, A, and W are as defined in the disclosure, or a salt thereof, or a hydrate or solvate thereof, and to processes for the preparation of these compounds and the therapeutic use thereof.

14 Claims, No Drawings

OTHER PUBLICATIONS

Sawyer, J. Scott et al., "Carbocyclic[g]indole Inhibitors of Human Nonpancreatic s-PLA2," Journal of Medicinal Chemistry (2005), vol. 48, pp. 893-896.

Marsais, F. et al., "Synthesis and Structural Study of 2,5-Dihydropyridines. Competitive Metalation of 2-Fluoropyridine," Journal of Organic Chemistry (1981), vol. 46, pp. 4494-4497.

Trecourt, Francois et al., "First Syntheses of Caerulomycin E and Collismycins A and C. A New Synthesis of Caerulomycin A," Journal of Organic Chemistry (1998), vol. 63, pp. 2892-2897.

Gooben, Lukas J. et al., "A Mild and Efficient Protocol for the Catalytic Silylation of Aryl Bromides," Synlett (2000), No. 12, pp. 1801-1803.

Pierrat, Philippe et al., "Unusual t-BuLi Induced Ortholithiation versus Halogen-Lithium Exchange in Bromopyridines: Two Alternative Strategies for Functionalization," Synlett (2004), No. 13, pp. 2319-2322.

Knittel, Dierk, "Verbesserte Synthese von a-Azidozimtsaure-estern und 2H-Azirinen," Synthesis (1985), pp. 186-188.

Pearson, Stuart E. et al., "A Practical, Efficient Synthesis of 5-Amino-7-azaindole," Synthesis (2005), No. 15, pp. 2503-2506.

Storz, Thomas et al., "The First Practical and Efficient One-Pot Synthesis of 6-Substituted 7-Azaindoles via a Reissert-Henze Reaction," Synthesis (2008), No. 2, pp. 0201-0214.

Trecourt, Francois et al., "New Syntheses of Substituted Pyridines via Bromine-Magnesium Exchange," Tetrahedron (2000), vol. 56, pp. 1349-1360.

Ye, Bao-Hui et al., "A novel method for the synthesis of regiospecifically sulfonated porphyrin monomers and dimers," Tetrahedron (2003), vol. 59, pp. 3593-3601.

Cabiddu, Maria G. et al., "Metallation reactions. Part 35: A change of the regiochemistry in the metallation of (alkylthio)arenes," Tetrahedron (2004), vol. 60, pp. 3915-3920.

Frissen, Aug. E. et al., "Novel Intramolecular Diels-Alder Reactions of Pyrimidines. Synthesis of Heterocyclic Annelated Pyridines," Tetrahedron Letters (1987), vol. 28, No. 14, pp. 1589-1592.

* cited by examiner

BICYCLIC DERIVATIVES OF AZABICYCLIC CARBOXAMIDES, PREPARATION THEREOF AND THERAPEUTIC USE THEREOF

Documents WO2006/024776, WO2006/072736, WO2007/010144 and WO2007/010138 describe bicyclic carboxamide derivatives with in vitro and in vivo antagonist or agonist activity on receptors of TRPV1 (or VR1) type.

There is still a need to find novel ligands for receptors of TRPV 1 type, which are improved in terms of functional activity, metabolic profile and/or safety profile.

The present invention satisfies this need by providing azabicyclic carboxamide derivatives that have in vitro and in vivo antagonist or agonist activity on receptors of TRPV1 (or VR1) type.

A first subject of the invention concerns the compounds corresponding to the general formula (I) hereinbelow.

Another subject of the invention concerns processes for preparing the compounds of general formula (I).

Another subject of the invention concerns the use of the compounds of general formula (I) especially in medicaments or in pharmaceutical compositions.

The compounds of the invention correspond to the general formula (I):

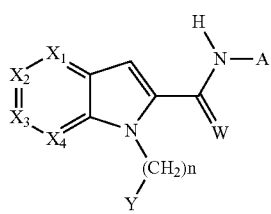
(I)

in which:

$X_1$, $X_2$, $X_3$ and $X_4$ represent, independently of each other, a nitrogen atom or a group $C-R_1$;

it being understood that when one from among $X_1$, $X_2$, $X_3$ and $X_4$ represents a nitrogen atom, the others correspond to a group $C-R_1$;

W represents an oxygen or sulfur atom;

n is equal to 0, 1, 2 or 3;

Y represents an aryl or a heteroaryl optionally substituted with one or more groups chosen from a halogen atom, a group $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, hydroxyl, $C_1$-$C_6$-alkoxy, $C_3$-$C_7$-cycloalkyloxy, $C_3$-$C_7$-cycloalkyl-$C_1$-$C_6$-alkylene-O—, $C_1$-$C_6$-fluoroalkoxy, cyano, C(O)NR$_4$R$_5$, nitro, NR$_4$R$_5$, $C_1$-$C_6$-thioalkyl, thiol, —S(O)—$C_1$-$C_6$-alkyl, —S(O)$_2$—$C_1$-$C_6$-alkyl, SO$_2$NR$_4$R$_5$, NR$_6$C(O)R$_7$, NR$_6$SO$_2$R$_8$, C(O)NR$_4$R$_5$, OC(O)NR$_4$R$_5$, —Si—($C_1$-$C_6$-alkyl)$_3$, —SF$_5$, aryl-$C_1$-$C_5$-alkylene or aryl, heteroaryl-$C_1$-$C_5$-alkylene or heteroaryl; the groups $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy and $C_3$-$C_7$-cycloalkyl-$C_1$-$C_6$-alkylene-O— being optionally substituted with a hydroxyl group, $C_1$-$C_6$-alkoxy or NR$_4$R$_5$, the aryl and heteroaryl groups being optionally substituted with one or more substituents R$_9$, which may be identical to or different from each other;

A represents the group of formula:

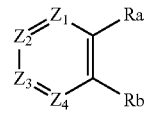

$Z_1$, $Z_2$, $Z_3$ and $Z_4$ represent, independently of each other, a nitrogen atom, a carbon atom or a group $C-R_2$, at least one from among $Z_1$, $Z_2$, $Z_3$ and $Z_4$ corresponding to a nitrogen atom and one from among $Z_1$, $Z_2$, $Z_3$ and $Z_4$, corresponding to a carbon atom, being bonded to the nitrogen atom of the amide or of the thioamide of formula (I);

Ra and Rb form, together with the carbon atoms that bear them, either a partially unsaturated cycloalkyl, or an aryl;

or a heterocycle, or a heteroaryl, which is 5- to 7-membered, comprising from 1 to 3 heteroatoms chosen from O, S and N;

it being understood that when Ra and Rb together form, with the carbon atoms that bear them, a 5-membered ring, this ring comprising a nitrogen atom and carbon atoms, this ring being partially saturated or unsaturated, is excluded;

this partially unsaturated cycloalkyl, this aryl, this heterocycle or this heteroaryl possibly being substituted with one or more substituents R$_3$;

R$_1$ is chosen from a hydrogen atom, a halogen atom and a group $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryloxy-$C_1$-$C_6$-alkyl, heteroaryloxy-$C_1$-$C_6$-alkyl, aryl-$C_1$-$C_3$-alkylenoxy-$C_1$-$C_6$-alkyl, heteroaryl-$C_1$-$C_3$-alkylenoxy-$C_1$-$C_6$-alkyl, arylthio-$C_1$-$C_6$-alkyl, heteroarylthio-$C_1$-$C_6$-alkyl, aryl-$C_1$-$C_3$-alkylene-thio-$C_1$-$C_6$-alkyl, heteroaryl-$C_1$-$C_3$-alkylene-thio-$C_1$-$C_6$-alkyl, $C_1$-$C_6$-alkoxy, $C_3$-$C_7$-cycloalkyloxy, $C_3$-$C_7$-cycloalkyl-$C_1$-$C_3$-alkylenoxy, $C_1$-$C_6$-fluoroalkoxy, cyano, C(O)NR$_4$R$_5$, nitro, NR$_4$R$_5$, $C_1$-$C_6$-thioalkyl, $C_3$-$C_7$-cycloalkylthio, $C_3$-$C_7$-cycloalkyl-$C_1$-$C_3$-alkylene-thio, —S(O)—$C_1$-$C_6$-alkyl, —S(O)—$C_3$-$C_7$-cycloalkyl, —S(O)—$C_1$-$C_3$-alkylene-$C_3$-$C_7$-cycloalkyl, $C_1$-$C_6$-alkyl-S(O)$_2$—, $C_1$-$C_6$-fluoroalkyl-S(O)$_2$—, $C_3$-$C_7$-cycloalkyl-S(O)$_2$—, $C_3$-$C_7$-cycloalkyl-$C_1$-$C_3$-alkylene-S(O)$_2$—, SO$_2$NR$_4$R$_5$, —Si—($C_1$-$C_6$-alkyl)$_3$, —SF$_5$, NR$_6$C(O)R$_7$, NR$_6$SO$_2$R$_8$, C(O)NR$_4$R$_5$, OC(O)NR$_4$R$_5$, aryl, heteroaryl, aryl-$C_1$-$C_5$-alkylene, heteroaryl-$C_1$-$C_5$-alkylene, aryloxy, arylthio, heteroaryloxy or heteroarylthio; the heteroaryl or aryl groups being optionally substituted with one or more substituents R$_9$, which may be identical to or different from each other;

R$_2$ represents a hydrogen atom, a halogen atom or a group $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy, $C_3$-$C_7$-cycloalkyl-$C_1$-$C_3$-alkylene-O—, hydroxyl, thiol or $C_1$-$C_6$-fluoroalkoxy;

R$_3$ represents, when it is borne by a carbon atom, a hydrogen atom or a hydroxyl, thiol, $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy, $C_3$-$C_7$-cycloalkyl-$C_1$-$C_3$-alkylenoxy, $C_1$-$C_6$-alkoxy-$C_1$-$C_3$-alkylene, $C_3$-$C_7$-cycloalkyloxy-$C_1$-$C_3$-alkylene, $C_3$-$C_7$-cycloalkyl-$C_1$-$C_3$-alkylenoxy-$C_1$-$C_3$-alkylene, C(O)NR$_4$R$_5$, C(O)O—$C_1$-$C_6$-alkyl, CO$_2$H, oxo or thio group; the groups $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy, $C_3$-$C_7$-cycloalkyl-$C_1$-$C_3$-alkylenoxy, $C_1$-$C_6$-alkoxy-$C_1$-$C_3$-alkylene, $C_3$-$C_7$-cycloalkyloxy-$C_1$-$C_3$-alkylene and $C_3$-$C_7$-cycloalkyl- $C_1$-$C_3$-alkylenoxy-$C_1$-$C_3$-alkylene possibly being substituted with a hydroxyl group, $C_1$-$C_6$-alkoxy, —OC(O)—$C_1$-$C_6$-alkyl or $NR_4R_5$;
or $R_3$ represents, when it is borne by a nitrogen atom, a hydrogen atom or a group $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl-C(O)—, $C_1$-$C_6$-alkyl-C(O)—, $C_3$-$C_7$-cycloalkyl-C(O)—, $C_3$-$C_7$-cycloalkyl-$C_1$-$C_3$-alkylene-C(O)—, $C_1$-$C_6$-fluoroalkyl-C(O)—, aryl-S(O), $C_1$-$C_6$-alkyl-S(O)—, $C_1$-$C_6$-fluoroalkyl-S(O)—, aryl-S(O)$_2$—, $C_1$-$C_6$-alkyl-S(O)$_2$—, $C_1$-$C_6$-fluoroalkyl-S(O)$_2$—, $C_3$-$C_7$-cycloalkyl-S(O)$_2$—, $C_3$-$C_7$-cycloalkyl-$C_1$-$C_3$-alkylene-S(O)$_2$—, $C_1$-$C_6$-alkyl-O—C(O)—, aryl-$C_1$-$C_3$-alkyl-O—C(O)—, $C_3$-$C_7$-cycloalkyl-O—C(O)—, $C_3$-$C_7$-cycloalkyl-$C_1$-$C_3$-alkylene-O—C(O)—, $C_1$-$C_6$-fluoroalkyl-β-C(O)—, aryl-O—C(O)—, heteroaryl-O—C(O)—, heteroaryl or aryl; the heteroaryl and aryl groups being optionally substituted with one or more substituents $R_9$, which may be identical to or different from each other; the groups $C_1$-$C_6$-alkyl, $C_3$-$C_7$-cycloalkyl, $C_3$-$C_7$-cycloalkyl-$C_1$-$C_3$-alkylene and $C_1$-$C_6$-fluoroalkyl possibly being substituted with a hydroxyl group, $C_1$-$C_6$-alkoxy or $NR_4R_5$;

$R_4$ and $R_5$, represent, independently of each other, a hydrogen atom or a group $C_1$-$C_6$-alkyl, $C_3$-$C_7$-cycloalkyl, $C_3$-$C_7$-cycloalkyl-$C_1$-$C_3$-alkylene, aryl-$C_1$-$C_5$-alkylene or aryl, or $R_4$ and $R_5$ together form, with the nitrogen atom that bears them, an azetidine, pyrrolidine, piperidine, azepine, morpholine, thiomorpholine, piperazine or homopiperazine group; the group $NR_4R_5$ being optionally substituted with a group $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene, aryl, heteroaryl, aryl-S(O)$_2$—, $C_1$-$C_6$-alkyl-S(O)$_2$—, $C_1$-$C_6$-fluoroalkyl-S(O)$_2$, $C_3$-$C_7$-cycloalkyl-S(O)$_2$—, $C_3$-$C_7$-cycloalkyl-$C_1$-$C_3$-alkylene-S(O)$_2$—, aryl-C(O)—, $C_1$-$C_6$-alkyl-C(O)—, $C_3$-$C_7$-cycloalkyl-C(O)—, $C_3$-$C_7$-cycloalkyl-$C_1$-$C_3$-alkylene-C(O)—, $C_1$-$C_6$-fluoroalkyl-C(O)—, hydroxyl, $C_1$-$C_6$-alkyloxy, $C_3$-$C_7$-cycloalkyloxy, $C_3$-$C_7$-cycloalkyl-$C_1$-$C_3$-alkylenoxy, $C_1$-$C_6$-fluoroalkyl, aryloxy-$C_1$-$C_6$-alkylene, aryloxy, heteroaryloxy-$C_1$-$C_6$-alkylene or heteroaryloxy;

$R_6$ and $R_7$ represent, independently of each other, a hydrogen atom or a group $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene or aryl; the aryl group being optionally substituted with one or more substituents chosen from a halogen atom and a group $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy, $C_3$-$C_7$-cycloalkyl-$C_1$-$C_3$-alkylenoxy, $C_1$-$C_6$-fluoroalkoxy, nitro or cyano;

or $R_6$ and $R_7$ together form a 4- to 7-membered lactam comprising the nitrogen atom and the C(O) group that bear them;

$R_8$ represents a group $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene or aryl; the aryl group being optionally substituted with one or more substituents chosen from a halogen atom and a group $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy, $C_3$-$C_7$-cycloalkyl-$C_1$-$C_3$-alkylenoxy, $C_1$-$C_6$-fluoroalkoxy, nitro or cyano;

or $R_6$ and $R_8$ together form a 4- to 7-membered sultam comprising the nitrogen atom and the S(O)$_2$ group that bear them;

$R_9$ represents a halogen atom or a group $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy, $C_3$-$C_7$-cycloalkyl-$C_1$-$C_3$-alkylenoxy or $C_1$-$C_6$-fluoroalkoxy; these groups being optionally substituted with a group OH, $C_1$-$C_6$-alkoxy or $NR_4R_5$; or alternatively $R_9$ represents a nitro, cyano or $NR_4R_5$ group.

In the compounds of general formula (I):
the sulfur atom(s) may be in oxidized form (S(O) or S(O)$_2$);
the nitrogen atom(s) may optionally be in oxidized form (N-oxide).

The compounds of formula (I) may comprise one or more asymmetric carbon atoms. They may thus exist in the form of enantiomers or diastereoisomers. These enantiomers and diastereoisomers, and also mixtures thereof, including racemic mixtures, form part of the invention.

The compounds of formula (I) may exist in the form of bases or of acid-addition salts. Such addition salts form part of the invention.

These solvents may be prepared with pharmaceutically acceptable acids, but the salts of other acids that are useful, for example, for purifying or isolating the compounds of formula (I) also form part of the invention.

The compounds of formula (I) may also exist in the form of hydrates or solvates, i.e. in the form of associations or combinations with one or more water molecules or with a solvent. Such hydrates and solvates also form part of the invention.

In the context of the present invention, the following definitions apply:
a halogen atom: a fluorine, a chlorine, a bromine or an iodine;

$C_t$-$C_z$: a carbon-based chain possibly containing from t to z carbon atoms in which t and z may take values from 1 to 7; for example, $C_1$-$C_3$ is a carbon-based chain possibly containing from 1 to 3 carbon atoms;

an alkyl: a linear or branched saturated aliphatic group. Examples that may be mentioned include methyl, ethyl, propyl, isopropyl, butyl, isobutyl, tert-butyl, pentyl, etc.;

an alkylene: a linear or branched saturated divalent alkyl group, for example a group $C_{1-3}$-alkylene represents a linear or branched divalent carbon-based chain of 1 to 3 carbon atoms, more particularly a methylene, ethylene, 1-methylthylene or propylene;

a cycloalkyl: a saturated or partially unsaturated cyclic alkyl group. Examples that may be mentioned include the groups cyclopropyl, cyclobutyl, cyclopentyl, cyclohexyl, cyclopropenyl, cyclobutenyl, cyclopentenyl, cyclohexenyl, etc.;

a cycloalkyloxy: a radical —O-cycloalkyl in which the cycloalkyl group is as defined previously;

a fluoroalkyl: an alkyl group, one or more hydrogen atoms of which have been replaced with a fluorine atom;

an alkoxy: a radical —O-alkyl in which the alkyl group is as defined previously;

a fluoroalkoxy: an alkoxy group, one or more hydrogen atoms of which have been replaced with a fluorine atom;

a thioalkyl or alkylthio: a radical —S-alkyl in which the alkyl group is as defined previously;

an aryl: a monocyclic or bicyclic aromatic group containing between 6 and 10 carbon atoms. Examples of aryl groups that may be mentioned include phenyl and naphthyl groups;

a heterocycle: a saturated or partially unsaturated 5- to 7-membered monocyclic group, comprising from 1 to 3 heteroatoms chosen from O, S and N.

Examples of heterocycles that may be mentioned include azetidinyl, piperidyl, azepinyl, morpholinyl, thiomorpholinyl, piperazinyl, homopiperazinyl, dihydrooxazolyl, dihydrothiazolyl, dihydroimidazolyl, dihydropyrrolyl or tetrahydropyridyl, [1,3]dioxolyl, [1,3]dioxinyl, dihydro[1,4]dioxinyl, dihydro[1,2]oxazinyl, dihydro[1,3]oxazinyl, dihydrooxazole, dihydroisoxazole, dihydro[1,4]oxazinyl, tetrahydro[1,3]oxazepinyl, tetrahydro[1,4]oxazepinyl, tetrahydro[1,3]diazepinyl and tetrahydro[1,4]diazepinyl.

a heteroaryl: a 5- to 12-membered monocyclic or bicyclic aromatic group containing from 1 to 5 heteroatoms chosen from O, S and N.

Examples of monocyclic heteroaryls that may be mentioned include imidazolyl, pyrazolyl, thiazolyl, oxazolyl, isothiazolyl, isoxazolyl, furyl, thienyl, oxadiazolyl, thiadiazolyl, triazolyl, tetrazolyl, pyridyl, pyrazinyl, pyrimidinyl, pyridazinyl and triazinyl.

Examples of bicyclic heteroaryls that may be mentioned include indolyl, isoindolyl, benzofuryl, benzothiophenyl, benzoxazolyl, benzimidazolyl, indazolyl, benzothienyl, isobenzofuryl, isobenzothiazolyl, pyrrolo[2,3-c]pyridyl, pyrrolo[2,3-b]pyridyl, pyrrolo[3,2-b]pyridyl, pyrrolo[3,2-c]pyridyl, pyrrolo[1,2-a]pyridyl, quinolyl, isoquinolyl, cinnolinyl, quinazolinyl, quinoxalinyl, pyrrolo[1,2-a]imidazolyl, imidazo[1,2-a]pyridyl, imidazo[1,2-a]pyridazinyl, imidazo[1,2-c]pyrimidinyl, imidazo[1,2-a]pyrimidinyl, imidazo[1,2-a]pyrazinyl, imidazo[4,5-b]pyrazinyl, imidazo[4,5-b]pyridyl, imidazo[4,5-c]pyridyl, pyrazolo[2,3-a]pyridyl, pyrazolo[2,3-a]pyrimidinyl, pyrazolo[2,3-a]pyrazinyl, thiazolo[5,4-b]pyridyl, thiazolo[5,4-c]pyridyl, thiazolo[4,5-c]pyridyl, thiazolo[4,5-b]pyridyl, oxazolo[5,4-b]pyridyl, oxazolo[5,4-c]pyridyl, oxazolo[4,5-c]pyridyl, oxazolo[4,5-b]pyridyl, isothiazolo[5,4-b]pyridyl, isothiazolo[5,4-c]pyridyl, isothiazolo[4,5-c]pyridyl, isothiazolo[4,5-b]pyridyl, isoxazolo[5,4-b]pyridyl, isoxazolo[5,4-c]pyridyl, isoxazolo[4,5-c]pyridyl and isoxazolo[4,5-b]pyridyl.

"oxo" means "=O";
"thio" means "=S".

Among the compounds of general formula (I) that are subjects of the invention, a first subgroup of compounds is constituted by the compounds for which $X_1$, $X_2$, $X_3$ and $X_4$ represent, independently of each other, a group $C-R_1$; $R_1$ being as defined in the general formula (I).

Among the compounds of general formula (I) that are subjects of the invention, a second subgroup of compounds is constituted by the compounds for which
$X_1$, $X_2$, $X_3$ and $X_4$ represent, independently of each other, a nitrogen atom or a group $C-R_1$;
it being understood that one from among $X_1$, $X_2$, $X_3$ and $X_4$ represents a nitrogen atom, the others representing a group $C-R_1$;
$R_1$ being as defined in the general formula (I).

Among the compounds of general formula (I) that are subjects of the invention, a third subgroup of compounds is constituted by the compounds for which
$X_1$, $X_2$ and $X_3$ represent a group $C-R_1$; $X_4$ represents a nitrogen atom;
$R_1$ being as defined in the general formula (I).

Among the compounds of general formula (I) that are subjects of the invention, a fourth subgroup of compounds is constituted by the compounds for which
$R_1$ is chosen from a hydrogen atom, a halogen atom and a group $C_1$-$C_6$-fluoroalkyl or $-Si(C_1$-$C_6$-alkyl$)_3$.

Among the compounds of general formula (I) that are subjects of the invention, a fifth subgroup of compounds is constituted by the compounds for which
$R_1$ is chosen from a hydrogen atom, a fluorine atom and a group $CF_3$ or $Si(CH_3)_3$.

Among the compounds of general formula (I) that are subjects of the invention, a sixth subgroup of compounds is constituted by the compounds for which $X_1$, $X_2$, $X_3$ and $X_4$ represent, independently of each other, a group $C-R_1$; $R_1$ is chosen from a hydrogen atom, a halogen atom and a group $C_1$-$C_6$-fluoroalkyl or $-Si-(C_1$-$C_6$-alkyl$)_3$.

Among the compounds of general formula (I) that are subjects of the invention, a seventh subgroup of compounds is constituted by the compounds for which
$X_1$, $X_2$ and $X_3$ represent a group $C-R_1$; $X_4$ represents a nitrogen atom;
$R_1$ is chosen from a hydrogen atom and a group $C_1$-$C_6$-fluoroalkyl.

Among the compounds of general formula (I) that are subjects of the invention, an eighth subgroup of compounds is constituted by the compounds for which n is equal to 1.

Among the compounds of general formula (I) that are subjects of the invention, a ninth subgroup of compounds is constituted by the compounds for which
Y represents an aryl or a heteroaryl optionally substituted with one or more groups chosen from a halogen atom and a group $C_1$-$C_6$-alkyl or $C_1$-$C_6$-fluoroalkyl.

Among the compounds of general formula (I) that are subjects of the invention, a tenth subgroup of compounds is constituted by the compounds for which
Y represents a phenyl, a thiazolyl or a pyridyl, this group being optionally substituted with one or more groups chosen from a halogen atom and a group $C_1$-$C_6$-alkyl or $C_1$-$C_6$-fluoroalkyl.

Among the compounds of general formula (I) that are subjects of the invention, an eleventh subgroup of compounds is constituted by the compounds for which
Y represents a phenyl, a thiazolyl or a pyridyl, this group being optionally substituted with one or more groups chosen from a fluorine atom and a methyl group or $CF_3$.

Among the compounds of general formula (I) that are subjects of the invention, a twelfth subgroup of compounds is constituted by the compounds for which
Y represents a phenyl optionally substituted with one or more groups chosen from a fluorine atom and a methyl group or $CF_3$.

Among the compounds of general formula (I) that are subjects of the invention, a thirteenth subgroup of compounds is constituted by the compounds for which W represents an oxygen atom.

Among the compounds of general formula (I) that are subjects of the invention, a fourteenth subgroup of compounds is constituted by the compounds for which
$Z_1$, $Z_2$, $Z_3$ and $Z_4$ represent, independently of each other, a nitrogen atom, a carbon atom or a group $C-R_2$,
one from among $Z_1$, $Z_2$, $Z_3$ and $Z_4$ corresponding to a nitrogen atom and
one from among $Z_1$, $Z_2$, $Z_3$ and $Z_4$, corresponding to a carbon atom, being bonded to the nitrogen atom of the amide or of the thioamide of formula (I);
and the two others from among $Z_1$, $Z_2$, $Z_3$ and $Z_4$ corresponding to a group $C-R_2$;
$R_2$ being as defined in the general formula (I).

Among the compounds of general formula (I) that are subjects of the invention, a fifteenth subgroup of compounds is constituted by the compounds for which
$Z_1$, $Z_2$, $Z_3$ and $Z_4$ represent, independently of each other, a nitrogen atom, a carbon atom or a group $C-R_2$,
one from among $Z_1$, $Z_2$, $Z_3$ and $Z_4$ corresponding to a nitrogen atom and
one from among $Z_1$, $Z_2$, $Z_3$ and $Z_4$, corresponding to a carbon atom, being bonded to the nitrogen atom of the amide or of the thioamide of formula (I);

and the two others from among $Z_1$, $Z_2$, $Z_3$ and $Z_4$ corresponding to a CH group.

Among the compounds of general formula (I) that are subjects of the invention, a sixteenth subgroup of compounds is constituted by the compounds for which
Ra and Rb together form, with the carbon atoms that bear them,
either a partially unsaturated cycloalkyl, or an aryl;
or a heterocycle, or a heteroaryl, which is 5- or 6-membered, comprising one or two heteroatoms chosen from O, S and N;
it being understood that when Ra and Rb together form, with the carbon atoms that bear them, a 5-membered ring, this ring comprising a nitrogen atom and carbon atoms, this ring being partially saturated or unsaturated, is excluded;
this partially unsaturated cycloalkyl, this aryl, this heterocycle or this heteroaryl possibly being substituted with one or more substituents $R_3$;
$R_3$ being as defined in the general formula (I).

Among the compounds of general formula (I) that are subjects of the invention, a seventeenth subgroup of compounds is constituted by the compounds for which
Ra and Rb together form, with the carbon atoms that bear them,
either a partially unsaturated cycloalkyl, or an aryl;
or a heterocycle, or a heteroaryl, which is 5- or 6-membered, comprising one or two heteroatoms chosen from O, S and N;
it being understood that when Ra and Rb together form, with the carbon atoms that bear them, a 5-membered ring, this ring comprising a nitrogen atom and carbon atoms, this ring being partially saturated or unsaturated, is excluded;
this partially unsaturated cycloalkyl, this aryl, this heterocycle or this heteroaryl possibly being substituted with one or more substituents $R_3$;
$R_3$ represents, when it is borne by a carbon atom, a hydrogen atom or a hydroxyl, $C_1$-$C_6$-alkyl or oxo group; the $C_1$-$C_6$-alkyl group possibly being substituted with a hydroxyl or —OC(O)—$C_1$-$C_6$-alkyl group;
or
$R_3$ represents, when it is borne by a nitrogen atom, a hydrogen atom or a group $C_1$-$C_6$-alkyl.

Among the compounds of general formula (I) that are subjects of the invention, an eighteenth subgroup of compounds is constituted by the compounds for which
Ra and Rb together form, with the carbon atoms that bear them,
either a partially unsaturated cycloalkyl, or an aryl;
or a heterocycle, or a heteroaryl, which is 5- or 6-membered, comprising one or two heteroatoms chosen from O, S and N;
it being understood that when Ra and Rb together form, with the carbon atoms that bear them, a 5-membered ring, this ring comprising a nitrogen atom and carbon atoms, this ring being partially saturated or unsaturated, is excluded;
this partially unsaturated cycloalkyl, this aryl, this heterocycle or this heteroaryl possibly being substituted with one or more substituents $R_3$;
$R_3$ represents, when it is borne by a carbon atom, a hydrogen atom or a hydroxyl, methyl or oxo group; the methyl groups possibly being substituted with a hydroxyl or —OC(O)-tert-butyl group;
or
$R_3$ represents, when it is borne by a nitrogen atom, a hydrogen atom or a methyl group.

Among the compounds of general formula (I) that are subjects of the invention, a nineteenth subgroup of compounds is constituted by the compounds for which A represents the group of formula:

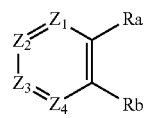

in which A is chosen from the groups

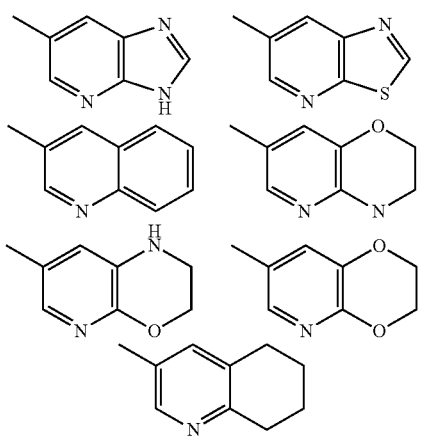

these groups being optionally substituted with $R_2$ and $R_3$ as defined in the general formula (I) hereinabove.

Among the compounds of general formula (I) that are subjects of the invention, a twentieth subgroup of compounds is constituted by the compounds for which A represents the group of formula:

in which A is chosen from the groups these groups being optionally substituted with $R_2$ and $R_3$ as defined in the general formula (I) hereinabove;
$R_2$ represents a hydrogen atom;
$R_3$ represents, when it is borne by a carbon atom, a hydrogen atom or a hydroxyl, $C_1$-$C_6$-alkyl or oxo group; the $C_1$-$C_6$- alkyl group possibly being substituted with a hydroxyl or —OC(O)—$C_1$-$C_6$-alkyl group;
or
$R_3$ represents, when it is borne by a nitrogen atom, a hydrogen atom or a group $C_1$-$C_6$-alkyl.

Among the compounds of general formula (I) that are subjects of the invention, a twenty-first subgroup of compounds is constituted by the compounds for which A represents the group of formula:

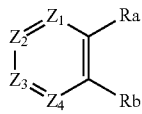

in which A is chosen from the groups

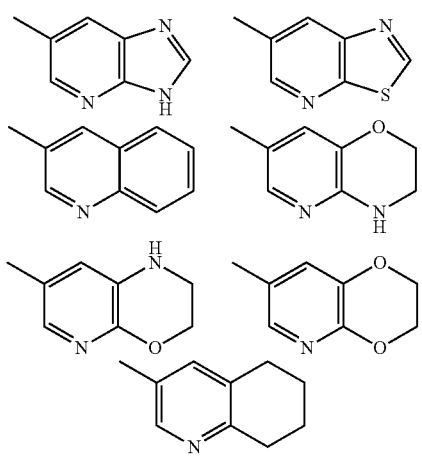

these groups being optionally substituted with $R_2$ and $R_3$ as defined in the general formula (I) hereinabove;
$R_3$ represents, when it is borne by a carbon atom, a hydrogen atom or a hydroxyl, methyl or oxo group; the methyl groups possibly being substituted with a hydroxyl or —OC(O)-tert-butyl group;
or
$R_3$ represents, when it is borne by a nitrogen atom, a hydrogen atom or a methyl group.

Among the compounds of general formula (I) that are subjects of the invention, a twenty-second subgroup of compounds is constituted by the compounds for which the definitions of $X_1$, $X_2$, $X_3$ and $X_4$, n, Y, W, $Z_1$, $Z_2$, $Z_3$, $Z_4$; Ra and Rb given hereinabove are combined.

Among the compounds of general formula (I) that are subjects of the invention, a twenty-third subgroup of compounds is constituted by the compounds for which $X_1$, $X_2$, $X_3$ and $X_4$ represent, independently of each other, a group C—$R_1$; or alternatively $X_1$, $X_2$ and $X_3$ represent a group C—$R_1$; $X_4$ represents a nitrogen atom;
$R_1$ is chosen from a hydrogen atom, a halogen atom and a group $C_1$-$C_6$-fluoroalkyl or —Si—($C_1$-$C_6$-alkyl)$_3$;
n is equal to 1;
Y represents an aryl or a heteroaryl optionally substituted with one or more groups chosen from a halogen atom and a group $C_1$-$C_6$-alkyl or $C_1$-$C_6$-fluoroalkyl;
W represents an oxygen atom;

A represents the group of formula:

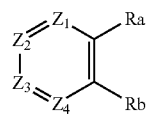

in which A is chosen from the groups

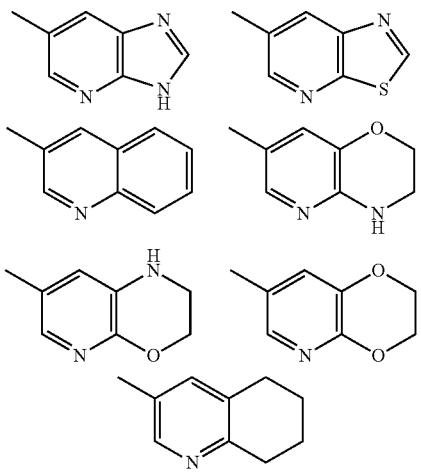

these groups being optionally substituted with $R_2$ and $R_3$ as defined in the general formula (I) hereinabove;
$R_2$ represents a hydrogen atom;
$R_3$ represents, when it is borne by a carbon atom, a hydrogen atom or a hydroxyl, $C_1$-$C_6$-alkyl or oxo group; the $C_1$-$C_6$-alkyl group possibly being substituted with a hydroxyl or —OC(O)—$C_1$-$C_6$-alkyl group;
or
$R_3$ represents, when it is borne by a nitrogen atom, a hydrogen atom or a group $C_1$-$C_6$-alkyl.

Among the compounds of general formula (I) that are subjects of the invention, a twenty-fourth subgroup of compounds is defined such that the compounds for which
$X_1$, $X_2$, $X_3$ and $X_4$ represent, independently of each other, a group C—$R_1$;
$R_1$ is chosen from a hydrogen atom, a halogen atom and a group $C_1$-$C_6$-alkyl, $C_1$-$C_6$-fluoroalkyl, $C_1$-$C_6$-alkoxy, $C_1$-$C_6$-fluoroalkoxy, $NR_4R_5$, $C_1$-$C_6$-thioalkyl, phenyl or isoxazolyl; the phenyl group being optionally substituted with one or more substituents $R_9$, which may be identical to or different from each other;
$R_4$ and $R_5$, represent, independently of each other, a hydrogen atom or a group $C_1$-$C_6$-alkyl,
W represents an oxygen atom;
n is equal to 0;
Y represents a phenyl optionally substituted with one or more substituents $R_9$, which may be identical to or different from each other; or Y represents an isoxazole;
$R_9$ represents a halogen atom or a group $C_1$-$C_6$-alkyl, $C_1$-$C_6$-alkoxy or cyano;

A represents the group D:

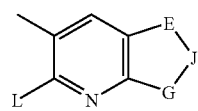

in which
L represents a hydrogen atom, a halogen atom or a group $C_1$-$C_4$-alkoxy;
the 5-membered ring is partially saturated or unsaturated; J represents N or C=O; E and G represent, independently of each other, an oxygen or sulfur atom, or a group C=O, $CH_2$ or N—R'; R' represents a hydrogen atom or a group $C_1$-$C_4$-alkyl or aryl-C(O)—, the aryl group being optionally substituted with one or more groups $C_1$-$C_6$-alkyl;
are excluded.

Among the compounds of general formula (I) that are subjects of the invention, one sub-family is represented by the compounds of general formula (I') for which:
$R_3$ represents, when it is borne by a carbon atom, a hydrogen atom or a hydroxyl, thiol, $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy, $C_3$-$C_7$-cycloalkyl-$C_1$-$C_3$-alkylenoxy, $C_1$-$C_6$-alkoxy-$C_1$-$C_3$-alkylene, $C_3$-$C_7$-cycloalkyloxy-$C_1$-$C_3$-alkylene, $C_3$-$C_7$-cycloalkyl-$C_1$-$C_3$-alkylenoxy-$C_1$-$C_3$-alkylene, C(O)$NR_4R_5$, C(O)O—$C_1$-$C_6$-alkyl, $CO_2H$, oxo or thio group; the groups $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy, $C_3$-$C_7$-cycloalkyl-$C_1$-$C_3$-alkylenoxy, $C_1$-$C_6$-alkoxy-$C_1$-$C_3$-alkylene, $C_3$-$C_7$-cycloalkyloxy-$C_1$-$C_3$-alkylene and $C_3$-$C_7$-cycloalkyl-$C_1$-$C_3$-alkylenoxy-$C_1$-$C_3$-alkylene possibly being substituted with a hydroxyl group, $C_1$-$C_6$-alkoxy or $NR_4R_5$.

Among the compounds of general formula (I') that are subjects of the invention, a first subgroup of compounds is constituted by the compounds for which $X_1$, $X_2$, $X_3$ and $X_4$ represent, independently of each other, a group C—$R_1$; and $R_1$ is chosen from a hydrogen atom and a halogen atom, more particularly a fluorine atom.

Among the compounds of general formula (I') that are subjects of the invention, a second subgroup of compounds is constituted by the compounds for which n is equal to 1 and Y represents an aryl, more particularly a phenyl, optionally substituted with one or more halogen atoms, more particularly fluorine atoms.

Among the compounds of general formula (I') that are subjects of the invention, a third subgroup of compounds is constituted by the compounds for which W represents an oxygen atom.

Among the compounds of general formula (I') that are subjects of the invention, a fourth subgroup of compounds is constituted by the compounds for which A represents the group of formula:

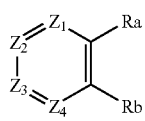

in which A is chosen from the groups

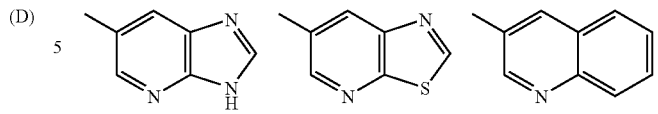

these groups being optionally substituted with $R_2$ and $R_3$ as defined in the general formula (I) hereinabove.

Among the compounds of general formula (I') that are subjects of the invention, a fifth subgroup of compounds is constituted by the compounds for which
$X_1$, $X_2$, $X_3$ and $X_4$ represent, independently of each other, a group C—$R_1$; and $R_1$ is chosen from a hydrogen atom and a halogen atom, more particularly a fluorine atom;
n is equal to 1;
Y represents an aryl, more particularly a phenyl, optionally substituted with one or more halogen atoms, more particularly fluorine atoms;
W represents an oxygen atom;
A represents the group of formula:

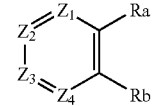

in which A is chosen from the groups

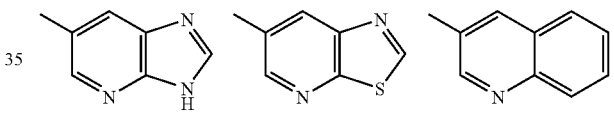

these groups being optionally substituted with $R_2$ and $R_3$ as defined in the general formula (I) hereinabove.

Among the compounds of general formula (I) that are subjects of the invention, mention may be made especially of the following compounds:
1  N-(2,3-Dimethyl-3H-imidazo[4,5-b]pyrid-6-yl)-5-fluoro-1-[(3-fluorophenyl)-methyl]-1H-indole-2-carboxamide;
2  N-(2-Methylthiazolo[5,4-b]pyrid-6-yl)-5-fluoro-1-[(3-fluorophenyl)methyl]-1H-indole-2-carboxamide;
3  N-(Thiazolo[5,4-b]pyrid-6-yl)-5-fluoro-1-[(3-fluorophenyl)methyl]-1H-indole-2-carboxamide;
4  N-(2-Hydroxymethylthiazolo[5,4-b]pyrid-6-yl)-5-fluoro-1-[(3-fluorophenyl)-methyl]-1H-indole-2-carboxamide;
5  N-(Quinol-3-yl)-5-fluoro-1-[(3-fluorophenyl)methyl]-1H-indole-2-carboxamide;
6  N-(2-Hydroxymethyl-3-methyl-3H-imidazo[4,5-b]pyrid-6-yl)-5-fluoro-1-[(3-fluorophenyl)methyl]-1H-indole-2-carboxamide;
7  N-(3-Methyl-3H-imidazo[4,5-b]pyrid-6-yl)-5-fluoro-1-[(3-fluorophenyl)methyl]-1H-indole-2-carboxamide;
8  N-(2,3-Dimethyl-3H-imidazo[4,5-b]pyrid-6-yl)-5-trifluoromethyl-1-[(3-fluoro-phenyl)methyl]-1H-pyrrolo[2,3-b]pyridine-2-carboxamide;
9  N-(3,4-Dihydro-2H-pyrido[3,2-b][1,4]oxazin-7-yl)-5-fluoro-1-[(3-fluorophenyl)-methyl]-1H-indole-2-carboxamide;
10  N-(4-Methyl-3,4-dihydro-2H-pyrido[3,2-b][1,4]oxazin-7-yl)-5-fluoro-1-[(3-fluoro-phenyl)methyl]-1H-indole-2-carboxamide;

11  N-(2-Methyl-3H-imidazo[4,5-b]pyrid-6-yl)-5-fluoro-1-[(3-fluorophenyl)methyl]-1H-indole-2-carboxamide;
12  N-(1-Methyl-2-oxo-2,3-dihydro-1H-pyrido[2,3-b][1,4]oxazin-7-yl)-5-fluoro-1-[(3-fluorophenyl)methyl]-1H-indole-2-carboxamide;
13  [6-[[[5-Fluoro-1-[(3-fluorophenyl)methyl]-1H-indol-2-yl]carbonyl]amino]thiazolo-[5,4-b]pyrid-2-yl]methyl 2,2-dimethylpropanoate;
14  N-(2,3-Dihydro-[1,4]dioxino[2,3-b]pyrid-7-yl))-5-fluoro-1-[(3-fluorophenyl)-methyl]-1H-indole-2-carboxamide;
15  N-(6-Hydroxy-5,6,7,8-tetrahydroquinol-3-yl)-5-fluoro-1-[(3-fluorophenyl)methyl]-1H-indole-2-carboxamide;
16  N-(2-Hydroxymethylthiazolo[5,4-b]pyrid-6-yl)-5-trifluoromethyl-1-[(3-methyl-phenyl)methyl]-1H-indole-2-carboxamide;
17  N-(2-Hydroxymethylthiazolo[5,4-b]pyrid-6-yl)-6-trifluoromethyl-1-[(3-methyl-phenyl)methyl]-1H-indole-2-carboxamide;
18  N-(2-Hydroxymethylthiazolo[5,4-b]pyrid-6-yl)-5-trimethylsilyl-1-[(3-methyl-phenyl)methyl]-1H-indole-2-carboxamide;
19  N-(2-Hydroxymethylthiazolo[5,4-b]pyrid-6-yl)-6-fluoro-1-[(3-methylphenyl)-methyl]-1H-indole-2-carboxamide;
20  N-(2-Hydroxymethylthiazolo[5,4-b]pyrid-6-yl)-5-trifluoromethyl-1-[(thiazol-2-yl)methyl]-1H-indole-2-carboxamide;
21  N-(2-Hydroxymethylthiazolo[5,4-b]pyrid-6-yl)-6-trifluoromethyl-1-[(thiazol-2-yl)methyl]-1H-indole-2-carboxamide;
22  N-(2-Hydroxymethylthiazolo[5,4-b]pyrid-6-yl)-5-trimethylsilyl-1-[(thiazol-2-yl)methyl]-1H-indole-2-carboxamide;
23  N-(2-Hydroxymethylthiazolo[5,4-b]pyrid-6-yl)-6-fluoro-1-[(thiazol-2-yl)methyl]-1H-indole-2-carboxamide;
24  N-(2-Hydroxymethylthiazolo[5,4-b]pyrid-6-yl)-5-trifluoromethyl-1-[(thiazol-2-yl)methyl]-1H-pyrrolo[2,3-b]pyridine-2-carboxamide;
25  N-(2-Hydroxymethylthiazolo[5,4-b]pyrid-6-yl)-6-trimethylsilyl-1-[(thiazol-2-yl)methyl]-1H-indole-2-carboxamide;
26  N-(2-Hydroxymethylthiazolo[5,4-b]pyrid-6-yl)-5-trifluoromethyl-1-[(pyrid-4-yl)methyl]-1H-indole-2-carboxamide;
27  N-(2-Hydroxymethylthiazolo[5,4-b]pyrid-6-yl)-6-trifluoromethyl-1-[(pyrid-4-yl)methyl]-1H-indole-2-carboxamide;
28  N-(2-Hydroxymethylthiazolo[5,4-b]pyrid-6-yl)-5-trimethylsilyl-1-[(pyrid-4-yl)-methyl]-1H-indole-2-carboxamide;
29  N-(2-Hydroxymethylthiazolo[5,4-b]pyrid-6-yl)-6-fluoro-1-[(pyrid-4-yl)methyl]-1H-indole-2-carboxamide;
30  N-(2-Hydroxymethylthiazolo[5,4-b]pyrid-6-yl)-5-trifluoromethyl-1-[(pyrid-4-yl)methyl]-1H-pyrrolo[2,3-b]pyridine-2-carboxamide;
31  N-(2-Hydroxymethylthiazolo[5,4-b]pyrid-6-yl)-6-trimethylsilyl-1-[(pyrid-4-yl)methyl]-1H-indole-2-carboxamide;
32  N-(2-Hydroxymethylthiazolo[5,4-b]pyrid-6-yl)-5-trimethylsilyl-1-[[(3-trifluoro-methyl)phenyl]methyl]-1H-indole-2-carboxamide;
33  N-(2-Hydroxymethylthiazolo[5,4-b]pyrid-6-yl)-6-fluoro-1-[[(3-trifluoromethyl)-phenyl]methyl]-1H-indole-2-carboxamide;
34  N-(2-Hydroxymethylthiazolo[5,4-b]pyrid-6-yl)-5-trifluoromethyl-1-[[(3-trifluoromethyl)phenyl]methyl]-1H-pyrrolo[2,3-b]pyridine-2-carboxamide;
35  N-(2-Hydroxymethylthiazolo[5,4-b]pyrid-6-yl)-6-trimethylsilyl-1-[[(3-trifluoromethyl)phenyl]methyl]-1H-indole-2-carboxamide;
36  N-(2-Hydroxymethylthiazolo[5,4-b]pyrid-6-yl)-5-trifluoromethyl-1-[(3-methyl-phenyl)methyl]-1H-pyrrolo[2,3-b]pyridine-2-carboxamide;
37  N-(2-Hydroxymethylthiazolo[5,4-b]pyrid-6-yl)-6-trimethylsilyl-1-[(3-methyl-phenyl)methyl]-1H-indole-2-carboxamide;
38  N-(2-Hydroxymethylthiazolo[5,4-b]pyrid-6-yl)-5-trifluoromethyl-1-[[(3-trifluoromethyl)phenyl]methyl]-1H-indole-2-carboxamide; and
39  N-(2-Hydroxymethylthiazolo[5,4-b]pyrid-6-yl)-6-trifluoromethyl-1-[[(3-trifluoromethyl)phenyl]methyl]-1H-indole-2-carboxamide.

In the text hereinbelow, the term "leaving group" means a group that can be readily cleaved from a molecule by breaking a heterolytic bond, with loss of an electron pair. This group may thus be readily replaced by another group during a substitution reaction, for example. Such leaving groups are, for example, halogens or an activated hydroxyl group such as a methanesulfonate, benzenesulfonate, p-toluenesulfate, triflate, acetate, etc. Examples of leaving groups and references for preparing them are given in "Advances in Organic Chemistry", J. March, 5th Edition, Wiley Interscience, 2001.

In the text hereinbelow, the term "protecting group" means a group that can be momentarily incorporated into a chemical structure for the purpose of temporarily inactivating a part of the molecule during a reaction, and which may be readily removed in a subsequent synthetic step. Examples of protecting groups and references concerning their properties are given in T. W. Greene, P. G. M. Wutz, 3rd Edition, Wiley Interscience 1999.

In accordance with the invention, the compounds of general formula (I) may be prepared according to the process illustrated by the general scheme 1 below:

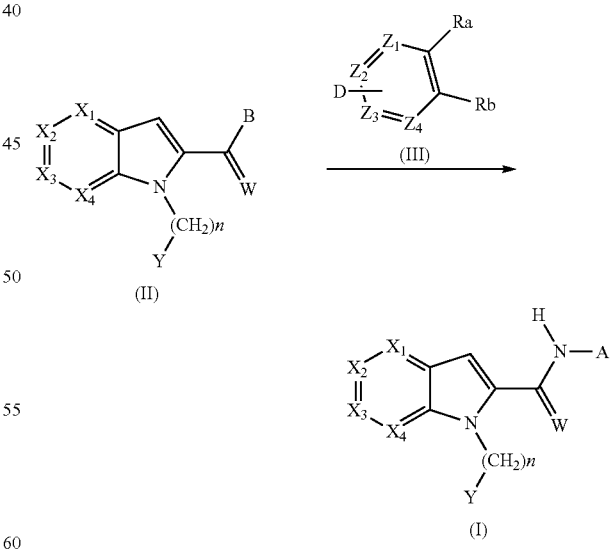

The compounds (I) may be obtained by reacting a compound of general formula (II), in which B corresponds to a hydroxyl group and $X_1$, $X_2$, $X_3$, $X_4$, n, Y and W are as defined in the general formula (I) hereinabove, with an amine of general formula (III), in which $Z_1$, $Z_2$, $Z_3$, $Z_4$, Ra and Rb are as defined in the general formula (I) hereinabove and D corresponds to an amino group, in the presence of a coupling agent such as a dialkylcarbodiimide, [(benzotriazol-1-yl) oxy][tris(pyrrolidino)]phosphonium hexafluoro-phosphate, diethyl cyanophosphonate or any other coupling agent known to those skilled in the art, optionally in the presence of a base such as triethylamine, in a solvent, for instance dimethylformamide.

Moreover, the compounds (I) may be obtained by reacting a compound of general formula (II), in which B represents a group $C_1$-$C_6$-alkoxy, $C_3$-$C_7$-cycloalkyloxy, $C_3$-$C_7$-cycloalkyl-$C_1$-$C_3$-alkylenoxy- or aryl-$C_1$-$C_3$-alkylenoxy and $X_1$, $X_2$, $X_3$, $X_4$, n, Y and W are as defined in the general formula hereinabove, with an amide of the compound of general formula (III), in which $Z_1$, $Z_2$, $Z_3$, $Z_4$, Ra and Rb are as defined in the general formula (I) hereinabove and D corresponds to an amino group, in a refluxing solvent such as toluene. The aluminium amide of the compound of general formula (III) is prepared via the prior action of trimethylaluminium on the amines of general formula (III).

The compounds (I) may also be obtained by reacting a compound of general formula (II), in which B corresponds to a chlorine atom and $X_1$, $X_2$, $X_3$, $X_4$, n, Y and W are as defined in the general formula (I) hereinabove, with an amine of general formula (III), in which $Z_1$, $Z_2$, $Z_3$, $Z_4$, Ra and Rb are as defined in the general formula (I) hereinabove and D corresponds to an amino group, by reaction in solution in a solvent such as dichloromethane or toluene. The compounds of general formula (II) in which B corresponds to a chlorine atom are prepared from compounds of general formula (II) in which B corresponds to a hydroxyl group, by reaction with a reagent such as thionyl chloride or oxalyl chloride, optionally in the presence of a base such as triethylamine, in solution in a solvent such as dichloromethane.

Starting with compounds of general formula (II), in which B represents an $NH_2$ group, W represents an oxygen atom and $X_1$, $X_2$, $X_3$, $X_4$, n and Y are as defined in the general formula (I) hereinabove, the compound of general formula (I) may be obtained by reaction with the compound of general formula (III), in which $Z_1$, $Z_2$, $Z_3$, $Z_4$, Ra and Rb are as defined in the general formula (I) hereinabove and D corresponds to a leaving group as defined hereinabove, such as a bromine atom or a triflate group, for example according to a method similar to that described in *J. Am. Chem. Soc.* 2001, 123 (31), 7727, or according to methods described in the literature or known to those skilled in the art, in the presence of a copper salt in catalytic amount, in the presence of a catalytic amount of a copper ligand, such as a diamine, the whole in the presence of a base such as potassium carbonate, in a solvent such as dioxane.

In Scheme 1, the compounds of general formula (I) and the other reagents, when their mode of preparation is not described, are commercially available, are described in the literature or are prepared by analogy with processes described in the literature (D. Knittel *Synthesis* 1985, 2, 186; T. M. Williams *J. Med. Chem.* 1993, 36 (9), 1291; JP2001-151771 A2, WO2006/024776, WO2006/072736, WO2007/010144, WO2007/010138 or WO2007/088277, for example).

The compounds of general formula (III), when their mode of preparation is not described, are commercially available, are described in the literature or are prepared by analogy with processes described in the literature (*Tetrahedron Lett.* 1987, 1589, *Synthesis* 2005, 15, 2503, *Synthesis* 2008, 2, 201, WO2006/040520).

The compounds of general formula (II) or (I), for which one from among $X_1$, $X_2$, $X_3$ and $X_4$ corresponds to a carbon atom substituted with an alkyl group, may be obtained via a coupling reaction, catalysed by a metal such as palladium or iron, performed on the corresponding compounds of general formula (II) or (I), substituted with a halogen atom, such as chlorine, in the presence, for example, of an alkylmagnesium halide or an alkylzinc halide, according to the methods described in the literature (A. Furstner et al. *J. Am. Chem. Soc.* 2002, 124(46), 13856; G. Queguiner et al., *J. Org. Chem.* 1998, 63(9), 2892) for example, or known to those skilled in the art.

The compounds of general formula (II) or (I), for which one from among $X_1$, $X_2$, $X_3$ and $X_4$ corresponds to a carbon atom substituted with a cyano, aryl or heteroaryl group, may be obtained via a coupling reaction, catalysed with a metal such as palladium, performed on the corresponding compounds of general formula (II) or (I), substituted, for example, with a bromine atom, in the presence of trimethylsilyl cyanide, an arylboronic acid or a heteroarylboronic acid, or via any other method described in the literature or known to those skilled in the art.

The compounds of general formula (I) or (II), for which one from among $X_1$, $X_2$, $X_3$ and $X_4$ corresponds to a carbon atom substituted with a group $NR_4R_5$, $NR_6COR_7$ or $NR_6SO_2R_8$, may be obtained from the corresponding compounds of general formula (I) or (II), substituted, for example, with a bromine atom, via a coupling reaction with, respectively, an amine, an amide or a sulfonamide in the presence of a base, a phosphine and a palladium-based catalyst, according to methods described in the literature or known to those skilled in the art.

The compounds of general formula (I) or (II) substituted with a group $C(O)NR_4R_5$ may be obtained from the corresponding compounds of general formula (I) or (II) substituted with a cyano group, according to methods described in the literature or known to those skilled in the art.

The compounds of general formula (I) or (II) substituted with a group —S(O)-alkyl or —S(O)$_2$-alkyl may be obtained via oxidation of the corresponding compounds of general formula (II) or (I), substituted with a thioalkyl group, according to methods described in the literature or known to those skilled in the art.

The compounds of general formula (II) or (I) substituted with a group $NR_4R_5$, $NR_6COR_7$ or $NR_6SO_2R_8$ may be obtained from the corresponding compounds of general formula (II) or (I), substituted with a nitro group, for example via reduction, followed by acylation or sulfonylation, according to methods described in the literature or known to those skilled in the art.

The compounds of general formula (II) or (I) substituted with a group $SO_2NR_4R_5$ may be obtained via a method similar to that described in *Pharmazie* 1990, 45, 346, or according to methods described in the literature or known to those skilled in the art.

The compounds of general formula (I) or (II) in which W represents a sulfur atom may be obtained, for example, by reacting the corresponding compounds of general formula (I) or (II), in which W represents an oxygen atom, with a reagent such as Lawesson's reagent.

The compounds of general formula (I) for which $R_3$ corresponds to a protecting group borne by a nitrogen atom, such as an acetyl, ethoxycarbonyl or tert-butyloxycarbonyl group or a benzyloxycarbonyl group, may be deprotected, according to chemical methods known to those skilled in the art, to give compounds of general formula (I) in which $R_3$ is a hydrogen atom.

The compounds of general formula (I), for which $R_3$ corresponds to a hydroxyalkyl group, may be obtained from the compounds of general formula (I) for which $R_3$ corresponds, for example, to an acetoxyalkyl or pivaloyloxyalkyl group according to chemical methods known to those skilled in the art, such as reaction with a base, for example aqueous sodium hydroxide solution, or reaction with an alkoxide, for example a methoxide, of a salt such as lithium or sodium, in an alcoholic solvent such as methanol or ethanol, or reaction with a reducing agent such as sodium borohydride, in a solvent such as tetrahydrofuran.

Alternatively, the compounds of general formula (I) for which $R_3$ corresponds to a hydroxyalkyl group may be obtained from the compounds of general formula (III), in which D corresponds to an amino group and $R_3$ corresponds, for example, to a pivaloyloxyalkyl group, by reaction with an organometallic reagent such as trimethylaluminium, followed by coupling with a compound of general formula (II), in which B corresponds to a group $C_1$-$C_6$-alkoxy, $C_3$-$C_7$-cycloalkyloxy, $C_3$-$C_7$-cycloalkyl-$C_1$-$C_3$-alkylenoxy- or aryl-$C_1$-$C_3$-alkylenoxy and $X_1$, $X_2$, $X_3$, $X_4$, n, Y and W are as defined in the general formula (I) hereinabove, followed by a treatment in acidic aqueous medium.

The compounds of general formula (II) of Scheme 1, in which one from among $X_1$, $X_2$, $X_3$ and $X_4$ represents a group C—$R_1$ in which $R_1$ corresponds to a group —Si—($C_1$-$C_6$-alkyl)$_3$ and B represents a group $C_1$-$C_6$-alkoxyl, may be obtained, for example, according to the methods illustrated in Scheme 2.

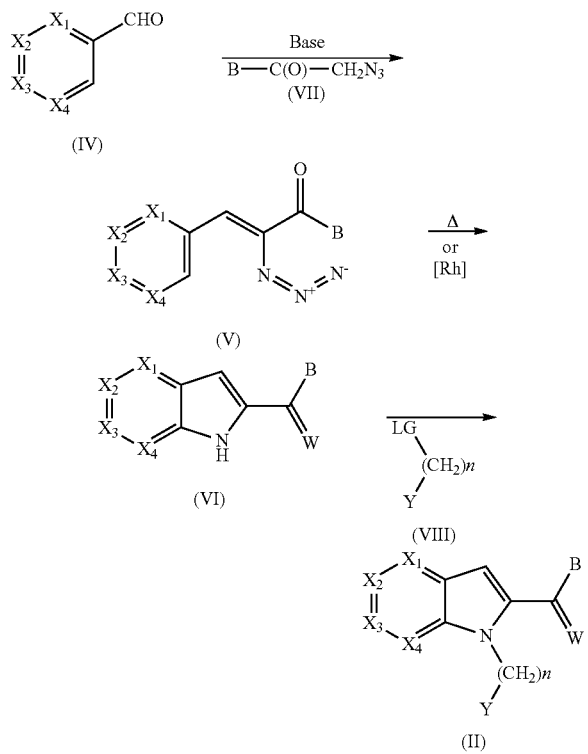

Scheme 2

According to this method, the compounds of general formula (II), defined such that n is equal to 1, 2 or 3, are obtained by reaction of the corresponding compounds (VI) with a reagent (VIII), in which LG represents a leaving group such as a chlorine, bromine or iodine atom and n is equal to 1, 2 or 3. The reaction for the formation of the compounds of general formula (II) may be performed in the presence of a base such as sodium hydride or potassium carbonate, in a polar solvent such as dimethylformamide, dimethyl sulfoxide or acetone (n=1: Kolasa T., Bioorg. Med. Chem. 1997, 5 (3) 507, n=2: Abramovitch R., Synth. Commun., 1995, 25 (1), 1).

When the compound of general formula (VIII) is defined such that n is equal to 1, 2 or 3 and LG represents a hydroxyl group, the compounds of general formula (II) may be obtained by reacting the compound of general formula (VI) with a compound of general formula (VIII) in the presence of a phosphine, for instance triphenylphosphine, and a reagent, for instance diethyl azodicarboxylate, dissolved in a solvent such as dichloromethane or tetrahydrofuran (O. Mitsonobu, Synthesis, 1981, 1-28).

Similarly, the compounds of general formula (II) may be obtained by reacting the compound of general formula (VI) with a compound of general formula (VIII) in the presence of a phosphine supported on a resin and of a reagent such as, for example, diisopropyl azodicarboxylate, dissolved in a solvent such as dichloromethane or tetrahydrofuran.

When the compound of general formula (VIII) is defined such that n is equal to 0 and LG represents a leaving group such as a chlorine, bromine or iodine atom, the reaction for formation of the compounds of general formula (II) may be performed by application or adaptation of the methods described by S. L. Buchwald et al. (*J. Am. Chem. Soc.*, 2001, 123, 7727 and 2002, 124, 11684), preferably under an inert atmosphere in basic medium, for example in the presence of potassium triphosphate, in the presence of a copper salt such as copper iodide, optionally in the presence of an additive such as N,N'-dimethylcyclohexane-1,2-diamine, the whole in an organic solvent such as toluene.

The compounds of general formula (VI) are prepared from aromatic or heteroaromatic aldehydes substituted with a silyl group of general formula (IV), in which $X_1$, $X_2$, $X_3$ and $X_4$ are as defined in the general formula (I) with one of them corresponding to a silyl group, by reaction with an alkyl azidoacetate of general formula (VII) in which B represents a group $C_1$-$C_6$-alkoxyl, for instance ethyl azidoacetate, in the presence of a base such as sodium ethoxide, in a solvent such as ethanol or methanol, to give the alkyl 2-azidocinnamates of general formula (V). These products are then converted into indole or azaindole esters in a refluxing solvent, for example in xylene or toluene, by adaptation of the protocols described in the literature (Hemetsberger et al. *Monatsh. Chem.*, 1969, 100, 1599 and 1970, 101, 161; P. Roy et al., *Synthesis.*, 2005, 16, 2751-2757; R. Guilard et al., *J. Heterocyclic. Chem.*, 1981, 18, 1365-1377; W. Rees et al., *J. Chem. Soc., Perkin Trans.* 1 1984, 2189-2196; P. Molina et al., *J. Org. Chem.*, 2003, 68(2), 489-499; C. Moody et al., *J. Chem. Soc., Perkin Trans.* 1 1984, 2189-2196; J. Sawyer et al., *J. Med. Chem.*, 2005, 48, 893-896; D. Tanner *Synlett* 2006, 18, 3140-3144).

Alternatively, the formation of the compounds of general formula (VI) may be obtained by decomposition of the alkyl 2-azidocinnamate of general formula (V), in the presence of a rhodium dimer complex, in a solvent such as toluene, at a temperature of between 25° C. and 60° C., according to an adaptation of protocols described in the literature (Tom G. Drivers et al., *J. Am. Chem. Soc.,* 2007, 129, 7500-7501; J. Sawyer et al., *J. Med. Chem.,* 2005, 48, 893-896).

The aromatic or heteroaromatic aldehydes substituted with a silyl group of general formula (IV), when they are not commercially available, may be obtained from the corresponding aromatic or heteroaromatic aldehydes, which are preferably masked in the form of an acetal, for example, substituted with a halogen atom such as a bromine or an iodine, in the position at which the silyl group is to be introduced:

for example by reaction with a disilane such as hexamethyldisilane, in the presence of a catalytic amount of a metal complex, preferably a palladium complex, for instance tetrakis(triphenylphosphine)palladium, without solvent or in a solvent, preferably a polar solvent, for instance hexamethylphosphoramide, in the presence of a base such as potassium carbonate, at a temperature of between 20° C. and the boiling point of the solvent (adaptation of the protocols described in the literature: J. Babin et al. *J. Organometall. Chem.*, 1993, 446 (1-2), 135-138; E. Shirakawa et al., *Chem. Commun.*, 2000, 1895-1896; L. Goossen et al. *Synlett*, 2000, 1801-1803; H. Matsumoto et al., *J. Organometall. Chem.*, 1975, 85, C1; FR 2 677 358).

for example by reaction with a disilane such as hexamethyldisilane, in the presence of a strong base, for instance hexamethylphosphorotriamide (HMPT), at a temperature close to 20° C. (adaptation of the protocols described in the literature: A. I. Meyers et al., *J. Org. Chem.*, 1977, 42 (15), 2654-2655; K. Ishimaru et al., *Heterocycles.*, 2001, 55 (8), 1591-1597).

The aromatic or heteroaromatic aldehydes substituted with a silyl group of general formula (IV), when they are not commercially available, may also be obtained from the corresponding dihalo aromatic or heteroaromatic derivatives, such as a dibromo derivative, in the position at which the silyl group is to be introduced, by exchange with an organometallic reagent, for instance n-butyllithium. The metallic aromatic or heteroaromatic derivatives thus formed may then react with organohalosilanes or may be converted into formyl derivatives by adaptation of the methods described in the literature. The reaction is preferably performed at low temperatures of between −110° C. and room temperature, in a solvent such as ether or THF (adaptation of the protocols described in the literature: Bao-Hui Ye et al., *Tetrahedron.*, 2003, 59, 3593-3601; P. Pierrat et al., *Synlett* 2004, 13, 2319-2322; K. T. Warner et al., *Heterocycles* 2002, 58, 383; D. Deffieux et al., *J. Organometall. Chem.*, 1994, 13 (6), 2415-2422; WO2005/080328; S. G. Davies et al., *J. Chem. Soc., Perkin Trans.* 1 1991, 501; G. Queguiner et al., *J. Org. Chem.*, 1981, 46, 4494-4497; G. Breton et al., *Tetrahedron* 2000, 56 (10), 1349-1360; S. De Montis et al., *Tetrahedron* 2004, 60 (17), 3915-3920; L. Buchwald et al., *J. Am. Chem. Soc.*, 1998, 120, 4960-4976).

According to another of its aspects, a subject of the invention is also the compounds of general formulae (IIa), (IIb), (IIc), (IId), (IIe), (IIf), (IIg) and (IIh), in which Me represents a methyl group and Et represents an ethyl group. These compounds are useful as intermediates for the synthesis of the compounds of formula (I).

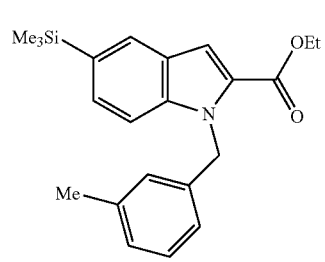

(IIa)

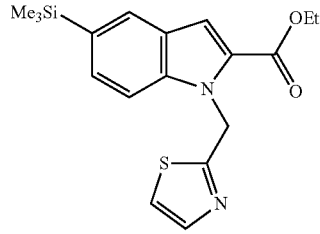

(IIb)

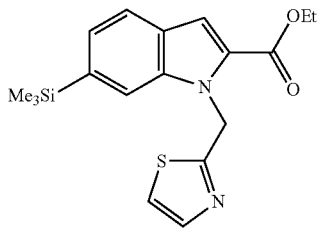

((IIc)

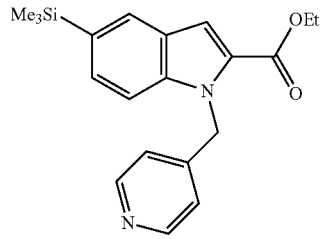

(IId)

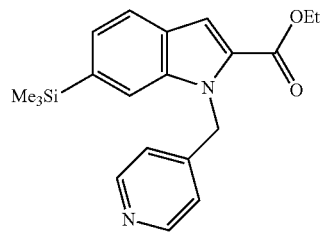

(IIe)

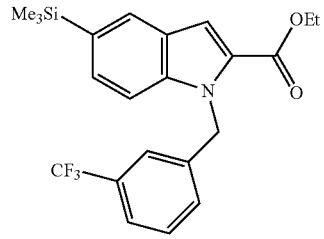

(IIf)

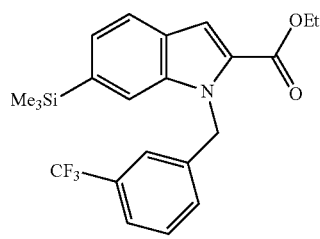

(IIg)

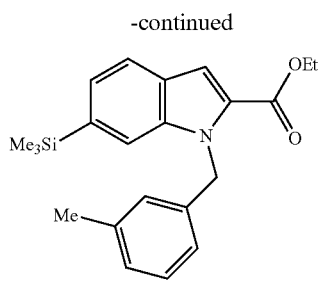

(IIh)

The esters (IIa), (IIb), (IIc), (IId), (IIe), (IIf), (IIg) and (IIh) are prepared according to the processes described in Examples 18, 22, 25, 28, 31, 32, 35 and 37.

The examples that follow describe the preparation of certain compounds in accordance with the invention. These examples are not limiting, and serve merely to illustrate the present invention. The numbers of the illustrated compounds refer to those in Table 1. The elemental microanalyses, the LC-MS analyses (liquid chromatography coupled to mass spectrometry) and the IR or NMR spectrum confirm the structures of the compounds obtained.

EXAMPLE 1

Compound 1

N-(2,3-Dimethyl-3H-imidazo[4,5-b]pyrid-6-yl)-5-fluoro-1-(3-fluorobenzyl)-1H-indole-2-carboxamide 1.1
5-Fluoro-1-(3-fluorobenzyl)-1H-indole-2-carboxylic acid Aqueous sodium hydroxide solution, prepared from 1.15 g (28.92 mmol) of sodium hydroxide pellets in 50 mL of water, is added to a solution of 7.6 g (24.10 mmol) of ethyl 5-fluoro-1-(3-fluorobenzyl)-1H-indole-2-carboxylate (WO2006/024776) in 241 mL of ethanol. The mixture is heated for 2 hours and then concentrated under reduced pressure. The resulting solid is taken up in 200 mL of water. The solution is washed with twice 100 mL of ethyl ether, acidified by successive addition of small amounts of concentrated hydrochloric acid and then extracted with 200 mL of ethyl acetate. The organic phase is finally washed twice with 100 mL of water and once with 50 mL of saturated sodium chloride solution, dried over magnesium sulfate and concentrated under reduced pressure. After drying at 50° C. under reduced pressure, 6.4 g of the expected product are obtained in the form of a solid, which is used without further purification in the rest of the synthesis.

1.2 N-(2,3-Dimethyl-3H-imidazo[4,5-b]pyrid-6-yl)-5-fluoro-1-(3-fluorobenzyl)-1H-indole-2-carboxamide (Compound 1)

To a solution, stirred at 20° C., of 0.25 g (0.87 mmol) of 5-fluoro-1-(3-fluorobenzyl)-1H-indole-2-carboxylic acid prepared in step 1.1, 183 mg (0.96 mmol) of N-(3-dimethylaminopropyl)-N'-ethylcarbodiimide hydrochloride (EDAC) and 129 mg (0.96 mmol) of 1-hydroxybenzotriazole (HOBT) in 8 mL of DMF are added 130 microliters (0.96 mol) of triethylamine and then 224 mg (1.13 mmol) of 6-amino-2,3-dimethyl-3H-imidazo[4,5-b]pyridine hydrochloride (*Ukrainskii Khimicheskii Zhurnal* 1981, 47, 867). The reaction mixture is stirred for 8 hours at 20° C. and then concentrated under reduced pressure. The resulting product is taken up in 100 mL of water, and a precipitate is collected by filtration and is purified by chromatography on a column of silica, eluting with a mixture of dichloromethane and methanol. The fractions containing the product are combined and evaporated to a quarter of their volume. 50 mL of n-heptane are added to the solution, and a solid is collected by filtration and dried under reduced pressure. 150 mg of the expected product are thus isolated.

m.p.=274-275° C.

$^1$H NMR (DMSO-D$_6$), δ ppm: 10.59 (s, 1H); 8.59 (s, 1H); 8.3 (s, 1H); 7.6 (m, 2H); 7.46 (s, 1H); 7.32 (m, 1H); 7.19 (m, 1H); 7.07 (m, 1H); 6.92 (m, 2H); 5.91 (s, 2H); 3.78 (s, 3H); 2.6 (s, 3H).

EXAMPLE 2

Compound 2

N-(2-Methylthiazolo[5,4-b]pyrid-6-yl)-5-fluoro-1-(3-fluorobenzyl)-1H-indole-2-carboxamide.

The process is performed according to a method similar to that of Example 1.2, starting with 0.5 g (1.74 mmol) of 5-fluoro-1-(3-fluorobenzyl)-1H-indole-2-carboxylic acid prepared in step 1.1 and 0.345 g (2.09 mmol) of 6-amino-2-methylthiazolo[5,4-b]pyridine (*Yakugaku Zasshi* 1950, 70, 187). At the end of the reaction, the product is concentrated under reduced pressure and then taken up in 100 mL of water. A precipitate is collected by filtration, and is purified by chromatography on a column of alumina, eluting with a mixture of dichloromethane and methanol. The resulting product is recrystallized from methanol, and a solid is collected by filtration, and dried under reduced pressure. 340 mg of the expected product are thus isolated.

m.p.=264-265° C.

$^1$H NMR (DMSO-D$_6$), δ ppm: 10.85 (s, 1H); 8.9 (s, 1H); 8.67 (s, 1H); 7.61 (m, 2H); 7.51 (s, 1H); 7.31 (m, 1H); 7.2 (m, 1H); 7.05 (m, 1H); 6.9 (m, 2H); 5.9 (s, 2H); 2.87 (s, 3H).

EXAMPLE 3

Compound 3

N-(Thiazolo[5,4-b]pyrid-6-yl)-5-fluoro-1-(3-fluorobenzyl)-1H-indole-2-carboxamide The process is performed according to a method similar to that of Example 1.2, starting with 0.32 g (1.11 mmol) of 5-fluoro-1-(3-fluorobenzyl)-1H-indole-2-carboxylic acid prepared in step 1.1 and 0.2021 g (1.34 mmol) of 6-aminothiazolo[5,4-b]pyridine (WO2007/100758). At the end of the reaction, the product is concentrated under reduced pressure and then taken up in 100 mL of water. A precipitate is collected by filtration, and is purified by chromatography on a column of alumina, eluting with a mixture of dichloromethane and methanol. The resulting product is recrystallized from methanol, and a solid is collected by filtration and dried under reduced pressure. 340 mg of the expected product are thus isolated.

m.p.=250-251° C.

$^1$H NMR (DMSO-D$_6$), δ ppm: 10.9 (s, 1H); 9.57 (s, 1H); 9 (s, 1H); 8.98 (s, 1H); 7.61 (m, 2H); 7.51 (s, 1H); 7.31 (m, 1H); 7.2 (m, 1H); 7.08 (m, 1H); 6.92 (m, 2H); 5.91 (s, 2H).

EXAMPLE 4

Compound 13

[6-[[[5-Fluoro-1-[(3-fluorophenyl)methyl]-1H-indol-2-yl]carbonyl]amino]thiazolo[5,4-b]pyrid-2-yl]methyl 2,2-dimethylpropanoate

4.1 (6-Nitrothiazolo[5,4-b]pyrid-2-yl)methyl 2,2-dimethylpropanoate

A mixture of 6 g (29.48 mmol) of 2-chloro-3,5-dinitropyridine and 7.74 g (44.22 mmol) of 2-amino-2-thioxoethyl pivalate in 50 mL of sulfolane is heated for 2 hours at 105° C. After this time, 150 mL of ethyl acetate are added to the mixture, and the organic phase is washed three times with 200 mL of water and then once with 100 mL of saturated sodium chloride solution. The organic phase is then separated out, dried over sodium sulfate and then concentrated under reduced pressure. The product obtained is purified by chromatography on a column of silica, eluting with a mixture of heptane and ethyl acetate. 1.45 g of a yellow solid are obtained.

$^1$H NMR (CDCl$_3$), δ ppm: 9.55 (d, 1H); 9.09 (d, 1H); 5.59 (s, 2H); 1.38 (s, 9H).

4.2 (6-Aminothiazolo[5,4-b]pyrid-2-yl)methyl 2,2-dimethyl propanoate

A mixture of 0.75 g (2.54 mmol) of (6-amino-thiazolo[5,4-b]pyrid-2-yl)methyl 2,2-dimethylpropanoate, prepared in step 4.1, and 1.68 g (8.89 mmol) of tin chloride in 50 mL of ethyl acetate is stirred for 30 minutes at 50° C. After this time, the reaction mixture is poured into 100 mL of ice-cold water. The pH of the aqueous solution is neutralized by successive addition of sodium hydroxide solution. The aqueous phase is then extracted with 3 times 50 mL of ethyl acetate. The organic phases are combined, dried and then concentrated under reduced pressure. 0.7 g of a solid is thus obtained, which product is used without further purification in the rest of the synthesis.

$^1$H NMR (CDCl$_3$), δ ppm: 8.05 (d, 1H); 7.42 (d, 1H); 5.37 (s, 2H); 1.21 (s, 9H).

4.3 [6-[[[5-Fluoro-1-[(3-fluorophenyl)methyl]-1H-indol-2-yl]carbonyl]amino]thiazolo-[5,4-b]pyrid-2-yl]methyl 2,2-dimethylpropanoate (Compound 13)

240 microliters (2.78 mmol) of oxalyl chloride are added, dropwise at 0° C., to a solution of 0.4 g (1.39 mmol) of 5-fluoro-1-[(3-fluorophenyl)methyl]-1H-indole-2-carboxylic acid, prepared in step 1.1, in 10 mL of dichloromethane and 0.5 mL of dimethylformamide. The mixture is stirred for 15 minutes at 0° C. and then for 1 hour at 20° C. After this time, a further 120 microliters (1.39 mmol) of oxalyl chloride are added and stirring is continued for 30 minutes at 20° C. The reaction mixture is then concentrated under reduced pressure and taken up in 5 mL of tetrahydrofuran. 219 microliters of triethylamine and then a solution of 0.44 g (1.67 mmol) of (6-amino-thiazolo[5,4-b]pyrid-2-yl)methyl 2,2-dimethylpropanoate, prepared in step 4.2, in 10 mL of tetrahydrofuran are added, under an inert atmosphere. The reaction mixture is stirred for 15 hours at 20° C. and for 1 hour at 40° C., and then concentrated under reduced pressure and taken up in 100 mL of water. The aqueous phase is extracted three times with 50 mL of ethyl acetate. The organic phases are combined, washed successively with 50 mL of saturated sodium hydrogen carbonate solution and with 50 mL of saturated sodium chloride solution, and then dried over sodium sulfate and concentrated under reduced pressure. The product thus obtained is purified on a column of alumina, eluting with dichloromethane. 0.15 g of the expected product is thus isolated.

m.p.=224-225° C.

$^1$H NMR (DMSO-D$_6$), δ ppm: 8.89 (s, 1H); 8.71 (s, 1H); 7.52 (m, 2H); 7.45 (s, 1H); 7.29 (m, 1H); 7.15 (m, 1H); 7.00 (m, 1H); 6.9 (m, 1H); 6.81 (m, 1H); 5.86 (s, 2H); 5.49 (s, 2H); 1.12 (s, 9H).

EXAMPLE 5

Compound 5

N-(Quinol-3-yl)-5-fluoro-1-(3-fluorobenzyl)-1H-indole-2-carboxamide 1.19 mL (2.38 mmol) of a 2M solution of trimethylaluminium in toluene are added dropwise to a solution, stirred at 0° C. under an inert atmosphere, of 0.274 g (1.9 mmol) of 3-aminoquinoline in 40 mL of dry toluene. The mixture is then stirred at 50° C. After 15 minutes, a solution of 0.5 g (1.59 mmol) of ethyl 5-fluoro-1-(3-fluorobenzyl)-1H-indole-2-carboxylate (WO2006/024776) in 10 mL of toluene is added dropwise. 15 mL of 1N hydrochloric acid solution and 100 mL of ethyl acetate are added to the mixture. The organic phase is separated out and then washed successively with 20 mL of 1N hydrochloric acid solution, 20 mL of water and 20 mL of saturated sodium chloride solution, and then concentrated under reduced pressure. The product thus obtained is triturated in 10 mL of hot toluene. A precipitate is collected by filtration. After drying, 295 mg of the expected product are thus isolated.

m.p.=244-246° C.

$^1$H NMR (CDCl$_3$), δ ppm: 10.91 (s, 1H); 9.15 (d, 1H); 8.88 (d, 1H); 8 (m, 2H); 7.62 (m, 5H); 7.32 (m, 1H); 7.21 (m, 1H); 7.08 (m, 1H); 6.92 (m, 2H); 5.95 (s, 2H).

EXAMPLE 6

Compound 4

N-(2-Hydroxymethylthiazolo[5,4-b]pyrid-6-yl)-5-fluoro-1-[(3-fluorophenyl)methyl]-1H-indole-2-carboxamide 50 mg (2.03 mmol) of sodium are added to 8 mL of methanol with stirring at 20° C. After 15 minutes, a solution of 0.15 g (0.28 mmol) of [6-[[[5-fluoro-1-[(3-fluorophenyl)methyl]-1H-indol-2-yl]carbonyl]amino]thiazolo[5,4-b]pyrid-2-yl]methyl 2,2-dimethylpropanoate (Compound 13), prepared in step 4.3, in 16 mL of methanol is added. Stirring is continued for 15 minutes at 20° C., and the reaction mixture is then concentrated under reduced pressure and taken up in 200 mL of molar ammonium chloride solution. The aqueous phase is extracted three times with 50 mL of ethyl acetate. The organic phases are combined, washed with 50 mL of saturated sodium chloride solution and then dried over sodium sulfate and concentrated under reduced pressure. The product thus obtained is purified on a column of silica, eluting with a mixture of dichloromethane and methanol. 70 mg of the expected product are thus isolated.

m.p.=225-226° C.

¹H NMR (CDCl₃), δ ppm: 10.84 (s, 1H); 8.92 (d, 1H); 8.72 (d, 1H); 7.61 (m, 2H); 7.5 (s, 1H); 7.35 (m, 1H); 7.2 (m, 1H); 7.08 (m, 1H); 6.92 (m, 2H); 6.37 (m, 1H); 5.91 (s, 2H); 4.9 (s, 2H).

EXAMPLE 7

Compound 6

N-(2-Hydroxymethyl-3-methyl-3H-imidazo[4,5-b]pyrid-6-yl)-5-fluoro-1-[(3-fluorophenyl)-methyl]-1H-indole-2-carboxamide

7.1 2-Hydroxymethyl-6-nitro-3-methyl-3H-imidazo[4,5-b]pyridine and 3-methyl-6-nitro-3H-imidazo[4,5-b]pyridine A mixture of 3.1 g (18.44 mmol) of 3-amino-5-nitro-2-methylaminopyridine and 3.5 g (46.09 mmol) of glycolic acid is heated at 150° C. After 75 minutes, the mixture is cooled and then dissolved in 50 mL of 1N hydrochloric acid. The pH of the aqueous phase is adjusted to 9 by successive additions of concentrated sodium hydroxide, and the mixture is then concentrated under reduced pressure. The resulting solid is purified by chromatography on a column of silica, eluting with a mixture of dichloromethane and methanol. 1.5 g of the expected product are thus isolated. This purification also allows 0.2 g of 3-methyl-6-nitro-3H-imidazo[4,5-b]pyridine to be isolated.

2-Hydroxymethyl-6-nitro-3-methyl-3H-imidazo[4,5-b]pyridine:

LCMS: [MH]⁺=209

¹H NMR (DMSO-D₆), δ ppm: 9.3 (d, 1H); 8.89 (d, 1H); 5.88 (m, 1H); 4.83 (m, 2H); 3.95 (t, 3H).

3-Methyl-6-nitro-3H-imidazo[4,5-b]pyridine:

LCMS: [MH]⁺=179

¹H NMR (DMSO-D₆), δ ppm: 9.31 (d, 1H); 8.95 (d, 1H); 8.79 (s, 1H); 3.95 (t, 3H).

7.2 6-Amino-2-hydroxymethyl-3-methyl-3H-imidazo[4,5-b]pyridine

A suspension of 0.5 g (2.4 mol) of 2-hydroxymethyl-6-nitro-3-methyl-3H-imidazo[4,5-b]pyridine, prepared in the preceding step, and 0.3 g of 10% palladium-on-charcoal is stirred for 3 hours under 2.5 atm. of hydrogen. After this time, the suspension is filtered through a pad of Celite and the filtrate is concentrated under reduced pressure. 0.4 g of the expected product is thus isolated, and is used without further purification in the rest of the synthesis.

LCMS: [MH]⁺=179

7.3 N-(2-Hydroxymethyl-3-methyl-3H-imidazo[4,5-b]pyrid-6-yl)-5-fluoro-1-[(3-fluorophenyl)methyl]-1H-indole-2-carboxamide (Compound 6)

Compound 6 is synthesized according to a process similar to that described in Example 1.2, starting with 6-amino-2-hydroxymethyl-3-methyl-3H-imidazo[4,5-b]-pyridine described in the preceding step and 5-fluoro-1-[(3-fluorophenyl)methyl]-1H-indole-2-carboxylic acid described in step 1.1.

m.p.: 231-232° C.

¹H NMR (DMSO-D₆), δ ppm: 10.67 (s, 1H); 8.68 (s, 1H); 8.4 (s, 1H); 7.6 (m, 2H); 7.48 (s, 1H); 7.33 (m, 1H); 7.18 (txd, 1H); 7.055 (txd, 1H); 6.94 (m, 2H); 5.92 (s, 2H); 5.69 (t, 1H); 4.8 (d, 2H); 3.88 (s, 3H)

EXAMPLE 8

Compound 7

N-(3-Methyl-3H-imidazo[4,5-b]pyrid-6-yl)-5-fluoro-1-[(3-fluorophenyl)methyl]-1H-indole-2-carboxamide

8.1 6-Amino-3-methyl-3H-imidazo[4,5-b]pyridine

This compound is prepared according to a process similar to that described in step 7.2, starting with 3-methyl-6-nitro-3H-imidazo[4,5-b]pyridine prepared in step 7.1.

LCMS: [MH]⁺=149

8.3 N-(3-Methyl-3H-imidazo[4,5-b]pyrid-6-yl)-5-fluoro-1-[(3-fluorophenyl)methyl]-1H-indole-2-carboxamide (Compound 7)

Compound 7 is synthesized according to a process similar to that described in Example 1.2, starting with 6-amino-3-methyl-3H-imidazo[4,5-b]pyridine, described in the preceding step, and 5-fluoro-1-[(3-fluorophenyl)methyl]-1H-indole-2-carboxylic acid, described in step 1.1.

m.p.: 235-236° C.

¹H NMR (DMSO-D₆), δ ppm: 10.68 (s, 1H); 8.69 (s, 1H); 8.42 (m, 2H); 7.6 (m, 2H); 7.49 (s, 1H); 7.32 (m, 1H); 7.19 (m, 1H); 7.06 (m, 1H); 6.92 (m, 2H); 5.91 (s, 2H); 3.87 (s, 3H).

EXAMPLE 9

Compound 8

N-(2,3-Dimethyl-3H-imidazo[4,5-b]pyrid-6-yl)-5-trifluoromethyl-1-[(3-fluorophenyl)-methyl]-1H-pyrrolo[2,3-b]pyridine-2-carboxamide This compound was prepared according to a process similar to that described in Example 1.2, starting with 5-trifluoromethyl-1-[(3-fluorophenyl)methyl]-1H-pyrrolo[2,3-b]pyridine-2-carboxylic acid (WO2008/093024).

m.p.: 274-275° C.

¹H NMR (DMSO-D₆), δ ppm: 10.75 (s, 1H); 8.83 (s, 1H); 8.76 (s, 1H); 8.55 (s, 1H); 8.28 (s, 1H); 7.63 (s, 1H); 7.32 (m, 1H); 7.07 (m, 1H); 6.98 (m, 2H); 6.01 (s, 2H); 3.76 (s, 3H); 2.6 (s, 3H).

EXAMPLE 10

Compound 9

N-(3,4-Dihydro-2H-pyrido[3,2-b][1,4]oxazin-7-yl)-5-fluoro-1-[(3-fluorophenyl)methyl]-1H-indole-2-carboxamide

10.1 5-Fluoro-1-[(3-fluorophenyl)methyl]-1H-indole-2-carboxamide

To a suspension, stirred at 20° C., of 2 g (6.96 mmol) of 5-fluoro-1-[(3-fluorophenyl)-methyl]-1H-indole-2-carboxylic acid, prepared in step 1.1, in 80 mL of dry toluene are added 5.08 mL (69.62 mmol) of thionyl chloride. The reaction mixture is stirred for 2 hours at reflux and is then concentrated under reduced pressure. The resulting product is taken up in 10 mL of dichloromethane, and this solution is poured dropwise into a solution of 9.12 mL (69.62 mmol) of 30% aqueous ammonia. The reaction mixture is stirred for 14 hours at 20° C. After this time, a solid is collected by filtration, and is triturated in 50 mL of diisopropyl ether. After filtering off and drying under reduced pressure, 0.58 g of the expected product is collected.

$^1$H NMR (DMSO-D$_6$), δ ppm: 8.11 (broad peak, 1H); 7.5 (m, 3H); 7.32 (m, 1H); 7.25 (s, 1H); 7.09 (m, 2H); 6.89 (m, 2H); 5.91 (s, 2H).

10.2 N-(3,4-Dihydro-2H-pyrido[3,2-b][1,4]oxazin-7-yl)-5-fluoro-1-[(3-fluorophenyl)-methyl]-1H-indole-2-carboxamide (Compound 9)

0.4 g (1.4 mmol) of the amide prepared in the preceding step, 0.31 g (1.47 mmol) of 7-bromo-3,4-dihydro-2H-pyrido[3,2-b][1,4]oxazine, 0.08 g (0.42 mmol) of copper iodide, 0.39 g (2.79 mmol) of potassium carbonate and 10 mL of dry dioxane are introduced into a pressure tube equipped with a magnetic stirrer. The suspension is degassed, 53 mg (0.46 mmol) of trans-1,2-cyclohexanediamine are added, and the tube is heated at 120° C. with stirring for 16 hours. After this time, 50 mL of ethyl acetate and 50 mL of water are added to the medium. The aqueous phase is separated out and then extracted with 2×30 mL of ethyl acetate. The organic phases are combined, washed with 50 mL of water, dried over sodium sulfate and then concentrated under reduced pressure. The resulting product is purified by chromatography on a column of silica, eluting with a mixture of heptane and ethyl acetate, followed by crystallization from a mixture of heptane and dichloromethane. 0.4 g of the expected product is thus isolated.

m.p.: 265-266° C.

$^1$H NMR (DMSO D$_6$), δ (ppm): 10.22 (s, 1H); 7.98 (s, 1H); 7.58 (m, 2H); 7.34 (m, 3H); 7.18 (m, 1H); 7.06 (m, 1H); 6.91 (m, 2H); 6.58 (s, 1H); 5.9 (s, 2H); 4.14 (m, 2H); 3.4 (m, 2H).

EXAMPLE 11

Compound 10

N-(4-Methyl-3,4-dihydro-2H-pyrido[3,2-b][1,4]oxazin-7-yl)-5-fluoro-1-[(3-fluorophenyl)-methyl]-1H-indole-2-carboxamide This compound was prepared according to a process similar to that described in Example 10.2, starting with 7-amino-4-methyl-3,4-dihydro-2H-pyrido[3,2-b][1,4]oxazine.

m.p.: 214-215° C.

$^1$H NMR (DMSO D$_6$), δ (ppm): 10.29 (s, 1H); 8.03 (s, 1H); 7.58 (m, 2H); 7.34 (m, 3H); 7.18 (m, 1H); 7.05 (m, 1H); 6.91 (m, 2H); 5.9 (s, 2H); 4.26 (m, 2H); 3.41 (m, 2H); 3.02 (s, 3H).

EXAMPLE 12

Compound 11

N-(2-Methyl-3H-imidazo[4,5-b]pyrid-6-yl)-5-fluoro-1-[(3-fluorophenyl)methyl]-1H-indole-2-carboxamide 12.1 2-Methyl-6-nitro-3H-imidazo[4,5-b]pyridine 2.3 mL (24.33 mol) of acetic anhydride are added to a solution, stirred at 15° C., of 1.5 g (9.73 mmol) of 2,3-diamino-5-nitropyridine in 15 mL of acetic acid. After stirring for 15 minutes at room temperature, the mixture is heated at 110° C. for 2 hours and then at 140° C. for 7 hours. The resulting mixture is concentrated under reduced pressure and taken up in 100 mL of water. A precipitate is collected by filtration. After purification by chromatography on a column of silica, 0.4 g of the expected product is obtained.

LCMS: [MH]$^+$=179

$^1$H NMR (DMSO D$_6$), δ (ppm): 9.2 (d, 1H); 8.7 (d, 1H); 2.62 (s, 3H).

12.2 6-Amino-2-methyl-3H-imidazo[4,5-b]pyridine

This compound is prepared according to a process similar to that described in step 7.2, starting with 2-methyl-6-nitro-3H-imidazo[4,5-b]pyridine prepared in step 12.1.

LCMS: [MH]$^+$=149

$^1$H NMR (DMSO D$_6$), δ (ppm): 7.7 (d, 1H); 6.99 (d, 1H); 2.4 (s, 3H).

12.3 N-(2-Methyl-3H-imidazo[4,5-b]pyrid-6-yl)-5-fluoro-1-[(3-fluorophenyl)methyl]-1H-indole-2-carboxamide (Compound 11)

This compound was prepared according to a process similar to that described in Example 1.2, starting with 5-fluoro-1-[(3-fluorophenyl)methyl]-1H-indole-2-carboxylic acid, prepared in Example 1.1 and 6-amino-2-methyl-3H-imidazo[4,5-b]pyridine, prepared in the preceding step.

m.p.: 299-300° C.

$^1$H NMR (DMSO D$_6$), δ (ppm): 12.37 (s, 1H); 10.6 (s, 1H); 8.53 (s, 1H); 8.29 (m, 1H); 7.61 (dxd, 1H); 7.58 (dxd, 1H); 7.46 (s, 1H); 7.33 (m, 1H); 7.18 (txd, 1H); 7.05 (txd, 1H); 6.94 (m, 2H); 5.9 (s, 2H); 2.48 (s, 3H).

EXAMPLE 13

Compound 12

N-(1-Methyl-2-oxo-2,3-dihydro-1H-pyrido[2,3-b][1,4]oxazin-7-yl)-5-fluoro-1-[(3-fluorophenyl)methyl]-1H-indole-2-carboxamide 13.1 7-Bromo-1-methyl-2-oxo-2,3-dihydro-1H-pyrido[2,3-b][1,4]oxazine 0.16 mL (2.62 mmol) of methyl iodide is added to a suspension of 0.5 g (2.18 mol) of 7-bromo-2-oxo-2,3-dihydro-1H-pyrido[2,3-b][1,4]oxazine, 0.24 g (1.09 mmol) of benzyltriethylammonium chloride and 0.75 g (5.46 mmol) of potassium carbonate in 25 mL of acetonitrile. The mixture is stirred for 6 hours at 60° C. After this time, a precipitate is removed by filtration. The filtrate is concentrated under reduced pressure and the resulting solid is taken up in 15 mL of dichloromethane and then washed successively with 20 ml of water, 10 mL of 0.1N hydrochloric acid solution, 10 mL of saturated sodium hydrogen carbonate solution and then 10 mL of water. After drying over sodium sulfate, the solution is finally concentrated under reduced pressure to give the expected product, which is used without further purification in the following step.

$^1$H NMR (DMSO D$_6$), δ (ppm): 7.98 (d, 1H); 7.79 (d, 1H); 4.9 (s, 2H); 3.29 (s, 3H).

13.2 N-(1-Methyl-2-oxo-2,3-dihydro-1H-pyrido[2,3-b][1,4]oxazin-7-yl)-5-fluoro-1-[(3-fluorophenyl)methyl]-1H-indole-2-carboxamide (Compound 12)

This compound was prepared according to a process similar to that described in Example 10.2, starting with 7-bromo- 1-methyl-2-oxo-2,3-dihydro-1H-pyrido[2,3-b][1,4]oxazine prepared in the preceding step.

m.p.: 248-250° C.

$^1$H NMR (DMSO D$_6$), δ (ppm): 10.61 (s, 1H); 8.23 (d, 1H); 7.91 (d, 1H); 7.59 (txd, 2H); 7.46 (s, 1H); 7.33 (m, 1H); 7.19 (txd, 1H); 7.06 (txd, 1H); 6.9 (m, 2H); 5.91 (s, 2H); 4.87 (s, 2H); 3.25 (s, 3H).

EXAMPLE 14

Compound 14

N-(2,3-Dihydro-[1,4]dioxino[2,3-b]pyrid-7-yl))-5-fluoro-1-[(3-fluorophenyl)methyl]-1H-indole-2-carboxamide This compound was prepared according to a process similar to that described in Example 10.2, starting with 7-bromo-2,3-dihydro-[1,4]dioxino[2,3-b]pyridine (WO2003/087098).

m.p.: 224-225° C.

$^1$H NMR (DMSO D$_6$), δ (ppm): 10.49 (s, 1H); 8.1 (s, 1H); 7.71 (s, 1H); 7.59 (m, 2H); 7.41 (s, 1H); 7.31 (m, 1H); 7.18 (m, 1H); 7.04 (m, 1H); 6.91 (m, 2H); 5.89 (s, 2H); 4.4 (m, 2H); 3.88 (m, 2H).

EXAMPLE 15

Compound 15

N-(6-Hydroxy-5,6,7,8-tetrahydroquinol-3-yl)-5-fluoro-1-[(3-fluorophenyl)methyl]-1H-indole-2-carboxamide This compound was prepared according to a process similar to that described in Example 1.2, starting with 3-amino-6-hydroxy-5,6,7,8-tetrahydroquinoline (WO2007/100758).

m.p.: 204-206° C.

$^1$H NMR (DMSO D$_6$), δ (ppm): 10.51 (s, 1H); 8.61 (s, 1H); 7.89 (s, 1H); 7.59 (m, 2H); 7.43 (s, 1H); 7.32 (m, 1H); 7.19 (m, 1H); 7.04 (m, 1H); 6.90 (m, 2H); 5.90 (s, 2H); 4.82 (d, 1H); 4.01 (m, 1H); 2.92 (m, 2H); 2.78 (m, 1H); 2.62 (m, 1H); 1.93 (m, 1H); 1.79 (m, 1H).

EXAMPLE 16

Compound 16

N-(2-Hydroxymethylthiazolo[5,4-b]pyrid-6-yl)-5-trifluoromethyl-1-[(3-methylphenyl)-methyl]-1H-indole-2-carboxamide 16.1 Ethyl 5-trifluoromethyl-1-[(3-methylphenyl)methyl]-1H-indole-2-carboxylate This compound was prepared by reacting 333 mg (1.295 mmol) of ethyl 5-trifluoromethyl-1H-indole-2-carboxylate with 0.31 mL (2.59 mmol) of 3-methylphenylmethanol in the presence of 0.92 g (3.826 mmol) of (cyanomethylene)tributylphosphorane (CMBP). The reaction mixture is stirred at 110° C. for 15 hours and then concentrated to dryness. The crude reaction product is then purified by flash chromatography on a column of silica gel in a mixture of heptane and ethyl acetate, to give 376 mg of the expected product in the form of an oil.

$^1$H NMR (DMSO D$_6$), δ (ppm): 8.18 (s, 1H); 7.81-7.78 (m, 1H); 7.61-7.57 (m, 1H), 7.53 (s, 1H); 7.14-7.12 (m, 2H); 7.01-6.91 (m, 1H); 6.75-6.73 (m, 1H); 5.88 (s, 2H); 4.31 (q, 2H); 2.21 (s, 3H); 1.30 (t, 3H).

LC-MS: 362([M+H]$^+$)

16.2 N-(2-Hydroxymethylthiazolo[5,4-b]pyrid-6-yl)-5-trifluoromethyl-1-[(3-methylphenyl)methyl]-1H-indole-2-carboxamide (Compound 16)

To a solution of 150 mg (0.415 mmol) of ethyl 5-trifluoromethyl-1-[(3-methylphenyl)methyl]-1H-indole-2-carboxylate prepared according to the protocol described in the preceding step and 132 mg (0.498 mmol) of (6-amino-thiazolo[5,4-b]pyrid-2-yl)methyl 2,2-dimethylpropanoate, obtained in step 4.2, in 1.5 mL of dry toluene, maintained under an inert atmosphere, is added dropwise, at 0° C., 0.31 mL (0.623 mmol) of a trimethylaluminium solution (2M/toluene). The reaction mixture is stirred at 110° C. for 15 hours and then concentrated to dryness. The crude reaction product is then diluted with normal hydrochloric acid solution. The product is extracted with ethyl acetate and then purified by chromatography on a column of silica, eluting with a mixture of heptane and ethyl acetate, to give 82 mg of the expected product.

m.p.: 315-316° C.

$^1$H NMR (DMSO D$_6$), δ (ppm): 10.97 (s, 1H); 8.92 (d, 1H); 8.70 (d, 1H); 8.22 (s, 1H); 7.81 (d, 1H); 7.62 (s, 1H); 7.60 (d, 1H); 7.14 (t, 1H); 7.03-6.97 (m, 2H); 6.87-6.84 (m, 1H), 6.38 (t, 1H); 5.91 (s, 2H); 4.87 (d, 2H); 2.19 (s, 3H).

EXAMPLE 17

Compound 17

N-(2-Hydroxymethylthiazolo[5,4-b]pyrid-6-yl)-6-trifluoromethyl-1-[(3-methylphenyl)-methyl]-1H-indole-2-carboxamide The product is prepared according to a process similar to that described in Example 16.

m.p.: 221-222° C.

$^1$H NMR (DMSO D$_6$), δ (ppm): 11.0 (s, 1H); 8.95 (s, 1H); 8.7 (s, 1H); 8.1 (s, 1H); 8.0 (d, 1H); 7.6 (s, 1H); 7.5 (d, 1H); 7.15 (t, 1H); 7.05 (m, 1H); 6.95 (s, 1H); 6.85 (m, 1H); 6.35 (t, 1H); 5.95 (s, 2H); 4.9 (d, 2H); 2.2 (s, 3H).

EXAMPLE 18

Compound 18

N-(2-Hydroxymethylthiazolo[5,4-b]pyrid-6-yl)-5-trimethylsilyl-1-[(3-methylphenyl)-methyl]-1H-indole-2-carboxamide 18.1 1-Bromo-3-trimethylsilylbenzene To a solution of 10 g (42.39 mmol) of 1,3-dibromobenzene in 80 mL of anhydrous Et$_2$O, cooled to −78° C. and maintained under a nitrogen atmosphere, are added dropwise with stirring, over 30 minutes, 26.49 mL (42.39 mmol) of a solution of BuLi (1.5M/hexane). After stirring for a further 30 minutes at −78° C., 5.96 mL (46.63 mmol) of TMSCl are added dropwise to the reaction mixture. Stirring is maintained at this temperature for 90 minutes and the reaction mixture is then hydrolysed by adding 15 mL of water. The product is extracted with ethyl acetate (3×50 mL). The combined organic phases are washed with saturated aqueous NaCl solution (2×25 mL), dried over Na$_2$SO$_4$, filtered and evaporated under reduced pressure. The crude reaction product is purified by chromatography on a column of silica gel, eluting with heptane, to give 9.3 g of the expected 1-bromo-3-trimethylsilylbenzene, in the form of a colourless oil.

$^1$H NMR (DMSO D$_6$), δ (ppm): 5.75 (s, 1H), 7.46 (m, 1H), 7.4 (m, 1H), 7.22 (t, 1H), 0.2 (s, 9H).

18.2 3-Trimethylsilylbenzaldehyde

To a solution of 5 g (21.89 mmol) of 1-bromo-3-trimethylsilylbenzene prepared according to the protocol described in the preceding step, in 40 mL of anhydrous Et$_2$O, cooled to 0° C. and maintained under a nitrogen atmosphere, are added dropwise, with stirring and over 30 minutes, 16.36 mL (26.18 mmol) of BuLi (1.6M/hexane). Stirring is continued at 0° C. for a further 30 minutes, and the mixture is then maintained at room temperature for 90 minutes. 2.69 mL (34.91 mmol) of DMF, diluted with 17 mL of anhydrous Et$_2$O, are then introduced into the reaction mixture. After stirring for 3 hours at room temperature, the reaction mixture is hydrolysed at 0° C. by successive addition of 10 mL of concentrated HCl solution and 100 mL of water. The product is extracted with 3×50 mL of CH$_2$Cl$_2$. The combined organic phases are washed with 100 mL of water, dried over Na$_2$SO$_4$, filtered and evaporated under reduced pressure. The crude reaction product is purified by flash chromatography on a column of silica gel, eluting with a gradient of from 10 to 20% of CH$_2$Cl$_2$ in heptane to give 1.82 g of the expected 3-trimethylsilylbenzaldehyde in the form of a yellow oil.

$^1$H NMR (DMSO D$_6$), δ (ppm): 10.01 (s, 1H); 8.0 (s, 1H); 7.85 (d, 1H); 7.8 (d, 1H); 7.5 (dd, 1H) 0.3 (s, 9H)

18.3 Ethyl 2-azido-3-(3-trimethylsilylphenyl)propenoate

To a solution of 2 g (87.5 mmol) of sodium in 30 mL of anhydrous EtOH, maintained under a nitrogen atmosphere and cooled to −10° C., is added, dropwise, a mixture of 31.4 mL (87.5 mmol) of ethyl azidoacetate (at 34% in CH$_2$Cl$_2$) and 3.9 g (21.87 mmol) of 3-trimethylsilylbenzaldehyde prepared according to the procedure described in the preceding step, diluted with 3 mL of EtOH. The reaction mixture is stirred at 0° C. for 4 hours. It is then hydrolysed by adding, with vigorous stirring, 100 mL of aqueous NH$_4$Cl solution (30%). The aqueous phase is extracted with 3×50 mL of EtOAc. The combined organic phases are washed with water, dried over Na$_2$SO$_4$ and concentrated under reduced pressure. The crude reaction product is purified by chromatography on a column of silica gel, eluting with an isocratic mixture of heptane and CH$_2$Cl$_2$ (80/20). 1.7 g of the expected ethyl 2-azido-3-(3-trimethylsilylphenyl)propenoate are thus isolated in the form of a yellow oil.

$^1$H NMR (DMSO D$_6$), δ (ppm): 7.9 (d, 1H); 7.8 (s, 1H); 7.4 (d, 1H); 7.3 (dd, 1H); 6.9 (s, 1H); 4.2 (q, 2H); 1.2 (t, 3H); 0.15 (s, 9H)

MS: [MH]$^+$=289

18.4 Ethyl 5-trimethylsilyl-1H-indole-2-carboxylate

To a solution of 1.7 g (5.90 mmol) of ethyl 2-azido-3-(3-trimethylsilylphenyl)propenoate prepared according to the procedure described in the preceding step, in 25 mL of dry toluene, maintained under an inert atmosphere, is added 0.62 g (0.59 mmol) of dirhodium (II) heptafluorobutyrate dimer complex. The reaction mixture is stirred for 7 hours at 40° C. A second portion of 0.62 g (0.59 mmol) of dirhodium (II) heptafluorobutyrate dimer complex is added to the reaction mixture while maintaining the stirring and heating at 40° C. for a further 1 hour. After cooling to room temperature, the reaction mixture is filtered through silica gel, eluting with toluene. The filtrate is then concentrated under reduced pressure. The greenish solid obtained is triturated several times in a minimum amount of heptane, until a white powder is obtained. This powder is dried under reduced pressure to give 0.87 g of the expected ethyl 5-trimethylsilyl-1H-indole-2-carboxylate in the form of a white powder.

m.p.=114-115° C.

$^1$H NMR (DMSO D$_6$), δ (ppm): 7.7 (s, 1H); 7.35 (d, 1H); 7.25 (d, 1H); 7.0 (s, 1H); 4.2 (q, 2H); 1.2 (t, 3H); 0.15 (s, 9H)

LC-MS: [MH]$^-$=260

18.5 Ethyl 5-trimethylsilyl-1-[(3-methylphenyl)methyl]-1H-indole-2-carboxylate (Compound IIa)

The product is prepared according to a process similar to that described in Example 16.1

$^1$H NMR (DMSO D$_6$), δ (ppm): 7.87 (s, 1H); 7.55 (d, 1H); 7.43 (d, 1H); 7.36 (s, 1H); 7.13 (t, 1H); 7.01 (d, 1H); 6.91 (s, 1H); 6.73 (d, 1H); 5.80 (s, 2H); 4.29 (q, 2H); 2.21 (s, 3H); 1.29 (t, 3H); 0.26 (s, 9H).

18.6 N-(2-Hydroxymethylthiazolo[5,4-b]pyrid-6-yl)-5-trimethylsilyl-1-[(3-methylphenyl)methyl]-1H-indole-2-carboxamide (Compound 18)

The product is prepared according to a process similar to that described in Example 16.2, starting with ethyl 5-trimethylsilyl-1-[(3-methylphenyl)methyl]-1H-indole-2-carboxylate (Compound IIa).

m.p.: 154-155° C.

$^1$H NMR (DMSO D$_6$), δ (ppm): 10.8 (s, 1H); 8.95 (s, 1H); 8.7 (s, 1H); 7.9 (s, 1H); 7.6 (d, 1H); 7.45 (s, 1H); 7.4 (d, 1H); 7.15 (t, 1H); 7.0 (m, 2H); 6.85 (d, 1H); 6.35 (t, 1H); 5.9 (s, 2H); 4.9 (d, 2H); 2.2 (s, 3H); 0.3 (s, 9H).

EXAMPLE 19

Compound 19

N-(2-Hydroxymethylthiazolo[5,4-b]pyrid-6-yl)-6-fluoro-1-[(3-methylphenyl)methyl]-1H-indole-2-carboxamide The product is prepared according to a process similar to that described in Example 16.

m.p.: 257-258° C.

$^1$H NMR (DMSO D$_6$), δ (ppm): 10.8 (s, 1H); 8.95 (s, 1H); 8.7 (s, 1H); 7.8 (m, 1H); 7.55 (s, 1H); 7.45 (d, 1H); 7.15 (t, 1H); 7.05 (m, 2H); 6.95 (s, 1H); 6.85 (m, 1H); 6.35 (t, 1H); 5.9 (s, 2H); 4.9 (d, 2H); 2.2 (s, 3H).

EXAMPLE 20

Compound 20

N-(2-Hydroxymethylthiazolo[5,4-b]pyrid-6-yl)-5-trifluoromethyl-1-[(thiazol-2-yl)methyl]-1H-indole-2-carboxamide 20.1 2-(Chloromethyl)thiazole To a solution of 0.5 g (4.34 mmol) of thiazol-2-ylmethanol in 5 mL of carbon tetrachloride and 6 mL of benzene are added 1.71 g (6.51 mmol) of triphenylphosphine. The reaction mixture is stirred at 95° C. for 2 hours. After cooling to room temperature, the reaction mixture is diluted with dichloromethane and then filtered through Celite. The filtrate is concentrated under reduced pressure and the residue obtained is purified by flash chromatography on a column of silica gel, eluting with a mixture of hexane and ethyl acetate, to give 0.4 g of the expected 2-(chloromethyl)thiazole in the form of a pale yellow oil.

$^1$H NMR (DMSO D$_6$), δ (ppm): 7.83-7.80 (m, 2H); 5.11 (s, 2H).

20.2 Ethyl 5-trifluoromethyl-1-[(thiazol-2-yl)]methyl-1H-indole-2-carboxylate To a suspension of 87 mg (1.983 mmol) of sodium hydride (55%) in 10 mL of dry DMF, maintained under an inert atmosphere, are added dropwise, at room temperature, 340 mg (1.322 mmol) of ethyl 5-trifluoromethyl-1H-indole-2-carboxylate in 5 mL of dry DMF. The reaction mixture is stirred at 50° C. for 1 hour. A solution of 265 mg (1.983 mmol) of 2-(chloromethyl)thiazole, prepared according to the protocol described in the preceding step, in 10 mL of THF is then added dropwise, at 0° C. The reaction mixture is then stirred for 20 hours at room temperature, and then diluted with 100 mL of ethyl acetate. The aqueous phase is extracted with 30 mL of ethyl acetate. The combined organic phases are washed successively with saturated aqueous sodium hydrogen carbonate solution, with water, with saturated aqueous sodium chloride solution and then dried over sodium sulfate, filtered and concentrated under reduced pressure. The resulting oil is purified by chromatography on a column of silica, eluting with a mixture of heptane and ethyl acetate. 265 mg of the expected product are isolated in the form of a colourless oil.

$^1$H NMR (DMSO D$_6$), δ (ppm): 8.18 (s, 1H); 7.95 (d, 1H); 7.72 (d, 1H); 7.65 (d, 1H); 7.62 (d, 1H); 7.54 (s, 1H); 6.20 (s, 2H); 4.34 (q, 2H); 1.31 (t, 3H).

LC-MS: 355 ([M+H]$^+$

20.3 N-(2-Hydroxymethylthiazolo[5,4-b]pyrid-6-yl)-5-trifluoromethyl-1-[(thiazol-2-yl)-methyl]-1H-indole-2-carboxamide (Compound 20)

This compound was prepared according to a process similar to that described in step 16.2, by reacting 125 mg (0.353 mmol) of ethyl 5-trifluoromethyl-1-[(thiazol-2-yl)methyl]-1H-indole-2-carboxylate, prepared according to the protocol described in the preceding step, with 94 mg (0.353 mmol) of (6-amino-thiazolo[5,4-b]pyrid-2-yl)methyl 2,2-dimethylpropanoate, obtained in step 4.2, in the presence of 0.26 mL (0.529 mmol) of a solution of trimethylaluminium (2M/toluene). The crude reaction product is then purified by flash chromatography on a column of silica gel, in a mixture of dichloromethane and methanol, and then washed with a mixture (1/1) of ether and dichloromethane, to give 64 mg of the expected product.

m.p.: 282-283° C.

$^1$H NMR (DMSO D$_6$), δ (ppm): 10.99 (s, 1H); 8.94 (d, 1H); 8.72 (d, 1H); 8.23 (s, 1H), 7.95 (d, 1H); 7.72-7.61 (m, 4H); 6.38 (t, 1H); 6.24 (s, 2H); 4.88 (d, 2H).

LC-MS: 490 ([M+H]$^+$

EXAMPLE 21

Compound 21

N-(2-Hydroxymethylthiazolo[5,4-b]pyrid-6-yl)-6-trifluoromethyl-1-[(thiazol-2-yl)methyl]-1H-indole-2-carboxamide The product is prepared according to a process similar to that described in Example 20.

m.p.: 243-244° C.

$^1$H NMR (DMSO D$_6$), δ (ppm): 11.0 (s, 1H); 8.95 (d, 1H); 8.7 (d, 1H); 8.2 (s, 1H); 8.0 (d, 1H); 7.75 (d, 1H); 7.6 (m, 2H); 7.5 (d, 1H); 6.35 (t, 1H); 6.25 (s, 2H); 4.9 (d, 2H).

EXAMPLE 22

Compound 22

N-(2-Hydroxymethylthiazolo[5,4-b]pyrid-6-yl)-5-trimethylsilyl-1-[(thiazol-2-yl)methyl]-1H-indole-2-carboxamide

22.1 Ethyl 5-trimethylsilyl-1-[(thiazol-2-yl)methyl]-1H-indole-2-carboxylate (Compound IIb)

This compound is prepared according to a process similar to that described in step 20.2, starting with ethyl 5-trimethylsilyl-1H-indole-2-carboxylate described in step 18.4.

$^1$H NMR (DMSO D$_6$), δ (ppm): 7.80 (s, 1H); 7.64 (d, 1H); 7.61 (d, 1H); 7.51 (d, 1H); 7.40 (d, 1H); 7.30 (s, 1H); 6.04 (s, 2H) 4.24 (q, 2H); 1.23 (t, 3H); 0.19 (s, 9H).

22.6 N-(2-Hydroxymethylthiazolo[5,4-b]pyrid-6-yl)-5-trimethylsilyl-1-[(thiazol-2-yl)-methyl]-1H-indole-2-carboxamide (Compound 22)

This compound is prepared according to a process similar to that described in step 16.2, starting with ethyl 5-trimethylsilyl-1-[(thiazol-2-yl)methyl]-1H-indole-2-carboxylate described in the preceding step.

m.p.: 270-271° C.

$^1$H NMR (DMSO D$_6$), δ (ppm): 10.8 (s, 1H); 8.95 (d, 1H); 8.7 (d, 1H); 7.9 (s, 1H); 7.7 (m, 2H); 7.55 (d, 1H); 7.5 (s, 1H); 7.45 (d, 1H); 6.35 (t, 1H); 6.2 (s, 2H); 4.9 (d, 2H); 0.3 (s, 9H).

EXAMPLE 23

Compound 23

N-(2-Hydroxymethylthiazolo[5,4-b]pyrid-6-yl)-6-fluoro-1-[(thiazol-2-yl)methyl]-1H-indole-2-carboxamide The product is prepared according to a process similar to that described in Example 20.

m.p.: 151-153° C.

$^1$H NMR (DMSO D$_6$), δ (ppm): 10.8 (s, 1H); 8.95 (d, 1H); 8.7 (d, 1H); 7.8 (m, 1H); 7.7 (d, 1H); 7.6 (m, 3H); 7.1 (m, 1H); 6.35 (t, 1H); 6.2 (s, 2H); 4.9 (d, 2H).

EXAMPLE 24

Compound 24

N-(2-Hydroxymethylthiazolo[5,4-b]pyrid-6-yl)-5-trifluoromethyl-1-[(thiazol-2-yl)methyl]-1H-pyrrolo[2,3-b]pyridine-2-carboxamide The product is prepared according to a process similar to that described in Example 20.

m.p.: 207-208° C.

$^1$H NMR (DMSO D$_6$), δ (ppm): 11.1 (s, 1H); 8.95 (d, 1H); 8.85 (s, 1H); 8.8 (s, 1H); 8.7 (s, 1H); 7.7 (m, 1H); 7.65 (d, 1H); 7.58 (d, 1H); 6.35 (t, 1H); 6.3 (s, 2H); 4.9 (d, 2H).

EXAMPLE 25

Compound 25

N-(2-Hydroxymethylthiazolo[5,4-b]pyrid-6-yl)-6-trimethylsilyl-1-[(thiazol-2-yl)methyl]-1H-indole-2-carboxamide

25.1 Ethyl 2-azido-3-(4-trimethylsilylphenyl)propenoate 1.26 g (54.96 mmol) of sodium and 30 mL of anhydrous ethanol are introduced into a 100 mL round-bottomed flask, equipped with a magnetic stirrer and maintained under a nitrogen atmosphere. The reaction mixture is stirred at room temperature until a homogeneous solution is obtained. To this solution, cooled to −10° C., is added dropwise a solution containing 16.83 mL (54.96 mmol) of ethyl azidoacetate (34% in $CH_2Cl_2$) and 5 g (27.48 mmol) of 4-trimethylsilyl-benzaldehyde in 5 mL of ethanol. The reaction mixture is then stirred at 0° C. for 4 hours. The reaction medium is hydrolysed by adding, with vigorous stirring, 100 mL of ammonium chloride solution (30% aqueous). The product is extracted with three times 50 mL of ethyl acetate. The combined organic phases are washed with twice 20 mL of water, dried over sodium sulfate and concentrated under reduced pressure. The resulting oil is purified by chromatography on a column of silica gel, eluting with a mixture of heptane and dichloromethane. 4.96 g of the expected product are isolated in the form of a yellow oil.

$^1$H NMR (DMSO $D_6$), δ (ppm): 7.6 (d, 2H); 7.35 (d, 2H); 6.7 (s, 1H); 4.1 (q, 2H); 1.1 (t, 3H); 0 (s, 9H).

25.2 Ethyl 6-trimethylsilyl-1H-indole-2-carboxylate

To a solution of 1.0 g (3.14 mmol) of ethyl 2-azido-3-(4-trimethylsilylphenyl)propenoate obtained in the preceding step, in 20 mL of dry toluene, maintained under an inert atmosphere, is added 0.17 g (0.16 mmol) of dirhodium (II) heptafluorobutyrate dimer complex. The reaction mixture is then stirred for 12 hours at 70° C. After cooling to room temperature, the reaction mixture is filtered through silica gel, eluting with ethyl acetate. The filtrate is then concentrated under reduced pressure. The residue is purified by chromatography on a column of silica gel, eluting with a mixture of heptane and dichloromethane. 0.61 g of the expected product is isolated in the form of a beige-coloured powder.

m.p.=127-129° C.

$^1$H NMR (DMSO $D_6$), δ (ppm): 11.7 (s, 1H); 7.41 (dd, 1H); 7.39 (d, 1H); 6.97 (dd, 1H); 6.88 (d, 1H); 4.1 (q, 2H); 1.1 (t, 3H); 0.0 (s, 9H).

25.3 Ethyl 6-trimethylsilyl-1-[(thiazol-2-yl)methyl]-1H-indole-2-carboxylate (Compound IIc)

This compound was prepared according to a process similar to that described in step 20.2, by reacting 570 mg (2.18 mmol) of ethyl 6-trimethylsilyl-1H-indole-2-carboxylate with 440 mg (3.27 mmol) of 2-(chloromethyl)thiazole in the presence of 0.14 g (3.27 mmol) of sodium hydride (55%). The crude reaction product is then purified by flash chromatography on a column of silica gel in a mixture of heptane and ethyl acetate, to give 520 mg of the expected product.

$^1$H NMR (DMSO $D_6$), δ (ppm): 7.76 (s, 1H); 7.65-7.61 (m, 2H); 7.52 (d, 1H); 7.28 (s, 1H); 7.22 (d, 1H); 6.09 (s, 2H); 4.23 (q, 2H); 1.22 (t, 3H); 0.2 (s, 9H).

LC-MS: 359 ([M+H]$^+$

25.4 N-(2-Hydroxymethylthiazolo[5,4-b]pyrid-6-yl)-6-trimethylsilyl-1-[(thiazol-2-yl)-methyl]-1H-indole-2-carboxamide (Compound 25)

This compound was prepared according to a process similar to that described in step 16.2, by reacting 200 mg (0.523 mmol) of ethyl 6-trimethylsilyl-1-[(thiazol-2-yl)]methyl-1H-indole-2-carboxylate, prepared in the preceding step, with 178 mg (0.670 mmol) of (6-amino-thiazolo[5,4-b]pyrid-2-yl)methyl 2,2-dimethylpropanoate, obtained in step 4.2, in the presence of 0.39 mL (0.784 mmol) of a solution of trimethylaluminium (2M/toluene). The product was isolated by purification by chromatography on a column of silica, eluting with a mixture of dichloromethane and ethanol. 120 mg of the expected product are obtained.

m.p.: 219-220° C.

$^1$H NMR (DMSO $D_6$), δ (ppm): 10.76 (s, 1H); 8.86 (d, 1H); 8.64 (d, 1H); 7.76 (s, 1H); 7.67 (d, 1H); 7.63 (d, 1H); 7.50 (d, 1H); 7.42 (s, 1H); 7.22 (d, 1H); 6.29 (t, 1H); 6.14 (s, 2H); 4.79 (d, 2H); 0.19 (s, 9H).

LC-MS: 494 ([M+H]$^+$

EXAMPLE 26

Compound 26

N-(2-Hydroxymethylthiazolo[5,4-b]pyrid-6-yl)-5-trifluoromethyl-1-[(pyrid-4-yl)methyl]-1H-indole-2-carboxamide The product is prepared according to a process similar to that described in Example 16.

m.p.: 237-238° C.

$^1$H NMR (DMSO $D_6$), δ (ppm): 8.9 (s, 1H); 8.7 (s, 1H); 8.5 (d, 2H); 8.3 (s, 1H); 7.8 (d, 1H); 7.75 (s, 1H); 7.6 (d, 1H); 7.0 (m, 2H); 6.35 (t, 1H); 6.0 (s, 2H); 4.9 (d, 2H).

EXAMPLE 27

Compound 27

N-(2-Hydroxymethylthiazolo[5,4-b]pyrid-6-yl)-6-trifluoromethyl-1-[(pyrid-4-yl)methyl]-1H-indole-2-carboxamide The product is prepared according to a process similar to that described in Example 16.

MP: 261-263° C.

$^1$H NMR (DMSO $D_6$), δ (ppm): 8.9 (s, 1H); 8.7 (s, 1H); 8.5 (d, 2H); 8.1 (m, 2H); 7.7 (s, 1H); 7.5 (d, 1H); 6.95 (d, 2H); 6.35 (t, 1H); 6.0 (s, 2H); 4.9 (d, 2H).

EXAMPLE 28

Compound 28

N-(2-Hydroxymethylthiazolo[5,4-b]pyrid-6-yl)-5-trimethylsilyl-1-[(pyrid-4-yl)methyl]-1H-indole-2-carboxamide

28.1 Ethyl 5-trimethylsilyl-1-[(pyrid-4-yl)methyl]-1H-indole-2-carboxylate (Compound IId)

The product is prepared according to a process similar to that described in Example 16.1, starting with ethyl 5-trimethylsilyl-1H-indole-2-carboxylate prepared in step 18.4.

¹H NMR (DMSO D₆), δ (ppm): 8.37 (d, 2H), 7.83 (s, 1H), 7.47 (d, 1H), 7.37 (d, 1H), 7.34 (s, 1H), 6.84 (d, 2H), 5.80 (s, 2H), 4.18 (q, 2H), 1.18 (t, 3H), 0.19 (s, 9H).

28.2 N-(2-Hydroxymethylthiazolo[5,4-b]pyrid-6-yl)-5-trimethylsilyl-1-[(pyrid-4-yl)-methyl]-1H-indole-2-carboxamide (Compound 28)

The product is prepared according to a process similar to that described in Example 16.2, starting with ethyl 5-trimethylsilyl-1-[(pyrid-4-yl)methyl]-1H-indole-2-carboxylate prepared in the preceding step.

m.p.: 208-210° C.

¹H NMR (DMSO D₆), δ (ppm): 8.9 (s, 1H); 8.7 (s, 1H); 8.45 (d, 2H); 7.95 (s, 1H); 7.58 (s, 1H); 7.5 (d, 1H); 7.4 (d, 1H); 7.0 (d, 2H); 6.35 (t, 1H); 5.9 (s, 2H); 4.9 (d, 2H); 0.3 (s, 9H).

EXAMPLE 29

Compound 29

N-(2-Hydroxymethylthiazolo[5,4-b]pyrid-6-yl)-6-fluoro-1-[(pyrid-4-yl)methyl]-1H-indole-2-carboxamide The product is prepared according to a process similar to that described in Example 16.

m.p.: 290-291° C.

¹H NMR (DMSO D₆), δ (ppm): 8.9 (s, 1H); 8.7 (s, 1H); 8.45 (d, 2H); 7.8 (m, 1H); 7.6 (s, 1H); 7.5 (dd, 1H); 7.1 (m, 1H); 7.0 (d, 2H); 6.35 (t, 1H); 5.9 (s, 2H); 4.9 (d, 2H).

EXAMPLE 30

Compound 30

N-(2-Hydroxymethylthiazolo[5,4-b]pyrid-6-yl)-5-trifluoromethyl-1-[(pyrid-4-yl)methyl]-1H-pyrrolo[2,3-b]pyridine-2-carboxamide

30.1 Ethyl 5-trifluoromethyl-1-[(4-pyridyl)methyl)]-1H-pyrrolo[2,3-b]pyrid-2-carboxylate This compound was prepared according to a process similar to that described in step 16.1, by reacting 480 mg (1.859 mmol) of ethyl 5-trifluoromethyl-1H-pyrrolo[2,3-b]pyrid-2-carboxylate with 406 mg (3.718 mmol) of 4-pyridylmethanol in the presence of 0.89 g (3.718 mmol) of cyanomethylenetributylphosphorane (CMBP). The crude reaction product is then purified by flash chromatography on a column of silica gel in a mixture of heptane and ethyl acetate, to give 582 mg of the expected product in the form of a white solid.

¹H NMR (DMSO D₆), δ (ppm): 8.84 (s, 1H); 8.72 (s, 1H); 8.45 (d, 2H); 7.56 (s, 1H); 6.98 (d, 2H); 5.94 (s, 2H); 4.29 (q, 2H); 1.25 (t, 3H).

LC-MS: 350 ([M+H]⁺

30.2 N-(2-Hydroxymethylthiazolo[5,4-b]pyrid-6-yl)-5-trifluoromethyl-1-[(pyrid-4-yl)-methyl]-1H-pyrrolo[2,3-b]pyridine-2-carboxamide (Compound 30)

This compound was prepared according to a process similar to that described in step 16.2, by reacting 200 mg (0.573 mmol) of ethyl 5-trifluoromethyl-1-[(4-pyridyl)methyl)]-1H-pyrrolo[2,3-b]pyrid-2-carboxylate, prepared according to the protocol described in the preceding step, with 182 mg (0.687 mmol) of (6-amino-thiazolo[5,4-b]pyrid-2-yl)-methyl 2,2-dimethylpropanoate, obtained in step 4.2, in the presence of 0.43 mL 0.859 mmol) of a solution of trimethylaluminium (2M/toluene). The crude reaction product is then purified by chromatography on a column of silica, eluting with a mixture of dichloromethane and methanol, to give 71 mg of the expected product.

m.p.: 275-276° C.

¹H NMR (DMSO D₆), δ (ppm): 11.03 (s, 1H); 8.89 (d, 1H); 8.82 (s, 2H); 8.65 (d, 1H); 8.45 (d, 2H); 7.74 (s, 1H); 7.04 (d, 2H); 6.38 (t, 1H); 5.99 (s, 2H); 4.87 (d, 2H).

LC-MS: 485 ([M+H]⁺

EXAMPLE 31

Compound 31

N-(2-Hydroxymethylthiazolo[5,4-b]pyrid-6-yl)-6-trimethylsilyl-1-[(pyrid-4-yl)methyl]-1H-indole-2-carboxamide

31.1 Ethyl 6-trimethylsilyl-1-[(pyrid-4-yl)methyl]-1H-indole-2-carboxylate (Compound IIe)

The product is prepared according to a process similar to that described in Example 16.1, starting with ethyl 6-trimethylsilyl-1H-indole-2-carboxylate prepared in step 25.2.

¹H NMR (DMSO D₆), δ (ppm): 8.2 (d, 2H); 7.49 (d, 1H); 7.42 (s, 1H); 7.15 (s, 1H); 7.05 (d, 1H); 6.70 (d, 2H); 5.68 (s, 2H); 4.01 (q, 2H); 1.01 (t, 3H); 0.0 (s, 9H).

31.2 N-(2-Hydroxymethylthiazolo[5,4-b]pyrid-6-yl)-6-trimethylsilyl-1-[(pyrid-4-yl)-methyl]-1H-indole-2-carboxamide (Compound 31)

The product is prepared according to a process similar to that described in Example 16.2, starting with ethyl 6-trimethylsilyl-1-[(pyrid-4-yl)methyl]-1H-indole-2-carboxylate prepared in the preceding step.

m.p.: 213-214° C.

¹H NMR (DMSO D₆), δ (ppm): 8.9 (s, 1H); 8.7 (s, 1H); 8.45 (d, 2H); 7.8 (d, 1H); 7.65 (s, 1H); 7.55 (s, 1H); 7.35 (d, 1H); 7.05 (d, 2H); 6.35 (t, 1H); 6.0 (s, 2H); 4.9 (d, 2H); 0.25 (s, 9H).

EXAMPLE 32

Compound 32

N-(2-Hydroxymethylthiazolo[5,4-b]pyrid-6-yl)-5-trimethylsilyl-1-[[(3-trifluoromethyl)-phenyl]methyl]-1H-indole-2-carboxamide

32.1 Ethyl 5-trimethylsilyl-1-[[(3-trifluoromethyl)phenyl]methyl]-1H-indole-2-carboxylate (Compound IIf)

The compound was prepared according to a process similar to that described in step 16.1, by reacting 0.49 g (1.87 mmol) of ethyl 5-trimethylsilyl-1H-indole-2-carboxylate, prepared in step 18.4, with 0.51 mL (3.749 mmol) of 3-(trifluoromethyl)phenylmethanol in the presence of 0.9 g (3.749 mmol) of cyanomethylenetributylphosphorane (CMBP). The crude reaction product is then purified by chromatography on a column of silica in a mixture of heptane and ethyl acetate, to give 730 mg of the expected product.

¹H NMR (DMSO D₆), δ (ppm): 7.90 (s, 1H); 7.62-7.57 (m, 2H); 7.51-7.43 (m, 3H); 7.40 (s, 1H); 7.17 (d, 1H); 5.92 (s, 2H); 4.28 (q, 2H); 1.26 (t, 3H); 0.27 (s, 9H).
LC-MS: 420 ([M+H]$^+$

32.2 N-(2-Hydroxymethylthiazolo[5,4-b]pyrid-6-yl)-5-trimethylsilyl-1-[[(3-trifluoro-methyl)phenyl]methyl]-1H-indole-2-carboxamide This compound was prepared according to a process similar to that described in step 16.2, by reacting 200 mg (0.477 mmol) of ethyl 5-trimethylsilyl-1-[[(3-trifluoromethyl)phenyl]methyl]-1H-indole-2-carboxylate, prepared in the preceding step, with 152 mg (0.572 mmol) of (6-amino-thiazolo[5,4-b]pyrid-2-yl)methyl 2,2-dimethylpropanoate, obtained in step 4.2, in the presence of 0.36 mL (0.715 mmol) of a solution of trimethylaluminium (2M/toluene). The product is isolated by purification by flash chromatography on a column of silica gel in a mixture of heptane and ethyl acetate. 128 mg of the expected product are obtained.
m.p.: 152-153° C.
¹H NMR (DMSO D₆), δ (ppm): 10.82 (s, 1H); 8.91 (d, 1H); 8.68 (d, 1H); 7.92 (s, 1H); 7.61-7.42 (m, 6H); 7.31 (d, 1H); 6.37 (t, 1H); 5.97 (s, 2H); 4.87 (d, 2H); 0.28 (s, 9H).
LC-MS: 555 ([M+H]$^+$

EXAMPLE 33

Compound 33

N-(2-Hydroxymethylthiazolo[5,4-b]pyrid-6-yl)-6-fluoro-1-[[(3-trifluoromethyl)phenyl]-methyl]-1H-indole-2-carboxamide

33.1 Methyl 6-fluoro-1-[(3-trifluoromethylphenyl)methyl]-1H-indole-2-carboxylate This compound was prepared according to a process similar to that described in step 16.1, by reacting 475 mg (2.459 mmol) of methyl 6-fluoro-1H-indole-2-carboxylate with 0.67 mL (4.918 mmol) of 3-trifluoromethylphenylmethanol in the presence of 1.18 g (4.918 mmol) of cyanomethylenetributylphosphorane (CMBP). The crude reaction product is then purified by chromatography on a column of silica in a mixture of heptane and ethyl acetate, to give 706 mg of the expected product in the form of a white solid.
¹H NMR (DMSO D₆), δ (ppm): 7.78 (dd, 1H); 7.61-7.49 (m, 4H); 7.43 (s, 1H); 7.19 (d, 1H); 7.05 (dt, 1H); 5.91 (s, 2H); 3.80 (s, 3H).
LC-MS: 351 ([M+H]$^+$

33.2 N-(2-Hydroxymethylthiazolo[5,4-b]pyrid-6-yl)-6-fluoro-1-[[(3-trifluoromethyl)-phenyl]methyl]-1H-indole-2-carboxamide (Compound 33)

This compound was prepared according to a process similar to that described in step 16.2, by reacting 200 mg (0.569 mmol) of methyl 6-fluoro-1-[(3-trifluoromethylphenyl)methyl]-1H-indole-2-carboxylate, prepared according to the protocol described in the preceding step, with 181 mg (0.683 mmol) of (6-amino-thiazolo[5,4-b]pyrid-2-yl)methyl 2,2-dimethylpropanoate, obtained in step 4.2, in the presence of 0.43 mL (0.853 mmol) of a solution of trimethylaluminium (2M/toluene). The crude reaction product is then purified by chromatography on a column of silica gel in a mixture of dichloromethane and methanol, to give 89 mg of the expected product.
m.p.: 217-218° C.
¹H NMR (DMSO D₆), δ (ppm): 10.81 (s, 1H); 8.89 (d, 1H); 8.67 (d, 1H); 7.82 (dd, 1H); 7.60-7.49 (m, 5H); 7.33 (d, 1H); 7.06 (dt, 1H); 6.37 (t, 1H); 5.95 (s, 2H); 4.87 (d, 2H).
LC-MS: 501 ([M+H]$^+$

EXAMPLE 34

Compound 34

N-(2-Hydroxymethylthiazolo[5,4-b]pyrid-6-yl)-5-trifluoromethyl-1-[[(3-trifluoromethyl)-phenyl]methyl]-1H-pyrrolo[2,3-b]pyridine-2-carboxamide The product is prepared according to a process similar to that described in Example 16.
m.p.: 312-314° C.
¹H NMR (DMSO D₆), δ (ppm): 11.0 (s, 1H); 8.90 (s, 1H); 8.85 (s, 1H); 8.8 (s, 1H); 8.65 (s, 1H); 7.7 (s, 1H); 7.6 (m, 2H); 7.5 (m, 1H); 7.35 (m, 1H); 6.35 (t, 1H); 6.05 (s, 2H); 4.9 (d, 2H).

EXAMPLE 35

Compound 35

N-(2-Hydroxymethylthiazolo[5,4-b]pyrid-6-yl)-6-trimethylsilyl-1-[[(3-trifluoromethyl)-phenyl]methyl]-1H-indole-2-carboxamide

35.1 Ethyl 6-trimethylsilyl-1-[[(3-trifluoromethyl)phenyl]methyl]-1H-indole-2-carboxylate (Compound IIg)

The product is prepared according to a protocol similar to that described in Example 32.1, starting with ethyl 6-trimethylsilyl-1H-indole-2-carboxylate described in Example 25.
¹H NMR (DMSO D₆), δ (ppm): 7.49-7.45 (m, 2H); 7.36-7.33 (m, 2H); 7.25 (t, 1H); 7.12 (s, 1H); 7.04-7.00 (m, 2H); 5.73 (s, 2H); 4.04 (q, 2H); 1.03 (t, 3H); 0.00 (s, 9H).

35.2 N-(2-Hydroxymethylthiazolo[5,4-b]pyrid-6-yl)-6-trimethylsilyl-1-[[(3-trifluoromethyl)phenyl]methyl]-1H-indole-2-carboxamide (Compound 35)

The product is prepared according to a process similar to that described in Example 32.2, starting with ethyl 6-trimethylsilyl-1-[[(3-trifluoromethyl)phenyl]methyl]-1H-indole-2-carboxylate prepared in the preceding step.
m.p.: 180-181° C.
¹H NMR (DMSO D₆), δ (ppm): 10.85 (s, 1H); 8.95 (s, 1H); 8.75 (s, 1H); 7.75 (m, 2H); 7.65 (s, 1H); 7.6-7.4 (m, 4H); 7.3 (d, 1H); 6.35 (t, 1H); 6.0 (s, 2H); 4.9 (d, 2H); 0.25 (s, 9H).

EXAMPLE 36

Compound 36

N-(2-Hydroxymethylthiazolo[5,4-b]pyrid-6-yl)-5-trifluoromethyl-1-[(3-methylphenyl)-methyl]-1H-pyrrolo[2,3-b]pyridine-2-carboxamide The product is prepared according to a process similar to that described in Example 16.
m.p.: 335-336° C.
¹H NMR (DMSO D₆), δ (ppm): 11.0 (s, 1H); 8.9 (s, 1H); 8.85 (s, 1H); 8.75 (s, 1H); 8.65 (s, 1H); 7.6 (s, 1H); 7.1 (m, 1H); 7.0 (m, 2H); 6.9 (m, 1H); 6.3 (t, 1H); 5.95 (s, 2H); 4.9 (d, 2H); 2.15 (s, 3H).

EXAMPLE 37

Compound 37

N-(2-Hydroxymethylthiazolo[5,4-b]pyrid-6-yl)-6-trimethylsilyl-1-[(3-methylphenyl)-methyl]-1H-indole-2-carboxamide 37.1 Ethyl 6-trimethylsilyl-1-[(3-methylphenyl)methyl]-1H-indole-2-carboxylate (Compound IIh)

The product is prepared according to a protocol similar to that described in Example 32.1, starting with ethyl 6-trimethylsilyl-1H-indole-2-carboxylate described in Example 25.

$^1$H NMR (DMSO D$_6$), δ (ppm): 7.71-7.68 (m, 2H); 7.33 (s, 1H); 7.24-7.21 (m, 1H); 7.14-7.11 (m, 2H); 7.09-7.0 (m, 1H); 6.81-6.79 (m, 1H); 5.85 (s, 2H); 4.30 (q, 2H); 2.21 (s, 3H); 1.17 (t, 3H), 0.25 (s, 9H).

37.2 N-(2-Hydroxymethylthiazolo[5,4-b]pyrid-6-yl)-6-trimethylsilyl-1-[(3-methylphenyl)methyl]-1H-indole-2-carboxamide (Compound 37)

The product is prepared according to a process similar to that described in Example 32.2, starting with ethyl 6-trimethylsilyl-1-[(3-methylphenyl)methyl]-1H-indole-2-carboxylate prepared in the preceding step.

m.p.: 168-169° C.

$^1$H NMR (DMSO D$_6$), δ (ppm): 10.8 (s, 1H); 8.9 (s, 1H); 8.7 (s, 1H); 7.7 (m, 2H); 7.48 (s, 1H); 7.25 (d, 1H); 7.15 (m, 1H); 7.0 (m, 2H); 6.9 (m, 1H); 6.35 (t, 1H); 5.9 (s, 2H); 4.9 (d, 2H); 2.2 (s, 3H); 0.3 (s, 9H).

EXAMPLE 38

Compound 38

N-(2-Hydroxymethylthiazolo[5,4-b]pyrid-6-yl)-5-trifluoromethyl-1-[[(3-trifluoromethyl)-phenyl]methyl]-1H-indole-2-carboxamide The product is prepared according to a process similar to that described in Example 16.

m.p.: 237-239° C.

$^1$H NMR (DMSO D$_6$), δ (ppm): 11.0 (s, 1H); 8.95 (s, 1H); 8.7 (s, 1H); 8.25 (s, 1H); 7.85 (d, 1H); 7.7 (s, 1H); 7.65-7.5 (m, 4H); 7.35 (m, 1H); 6.35 (t, 1H); 6.0 (s, 2H); 4.9 (d, 2H).

EXAMPLE 39

Compound 39

N-(2-Hydroxymethylthiazolo[5,4-b]pyrid-6-yl)-6-trifluoromethyl-1-[[(3-trifluoromethyl)-phenyl]methyl]-1H-indole-2-carboxamide The product is prepared according to a process similar to that described in Example 16.

m.p.: 197-198° C.

$^1$H NMR (DMSO D$_6$), δ (ppm): 11.0 (s, 1H); 8.95 (s, 1H); 8.7 (s, 1H); 8.15 (s, 1H); 8.05 (d, 1H); 7.65-7.45 (m, 5H); 7.35 (m, 1H); 6.35 (t, 1H); 6.1 (s, 1H); 4.9 (d, 2H).

Table I that follows illustrates the chemical structures and the physical properties of a number of examples of compounds according to the invention.

In this table:
the column "m.p. (° C.)" indicates the melting points of the products in degrees Celsius (° C.);
W represents an oxygen atom;
n is equal to 1;
all the compounds are in the form of the free base;
Me corresponds to a methyl group;
tBu corresponds to a tert-butyl group.

TABLE 1

(I)

| No. | X$_1$, X$_2$, X$_3$, X$_4$ | Y | A | m.p. (° C.) |
|---|---|---|---|---|
| 1 | CH, C—F, CH, CH | 3-fluorophenyl | 2-methyl-3-methyl-imidazo[4,5-b]pyridin-6-yl | 274-275 |
| 2 | CH, C—F, CH, CH | 3-fluorophenyl | 2-methylthiazolo[5,4-b]pyridin-6-yl | 264-265 |
| 3 | CH, C—F, CH, CH | 3-fluorophenyl | thiazolo[5,4-b]pyridin-6-yl | 250-251 |

TABLE 1-continued (I)

| No. | $X_1, X_2, X_3, X_4$ | Y | A | m.p. (° C.) |
|---|---|---|---|---|
| 4 | CH, C—F, CH, CH | 3-F-phenyl | 6-methyl-thiazolo[5,4-b]pyridin-2-yl-CH$_2$OH | 225-226 |
| 5 | CH, C—F, CH, CH | 3-F-phenyl | 3-methyl-quinolin-?-yl | 244-246 |
| 6 | CH, C—F, CH, CH | 3-F-phenyl | 6-methyl-3-methyl-imidazo[4,5-b]pyridin-2-yl-CH$_2$OH | 231-232 |
| 7 | CH, C—F, CH, CH | 3-F-phenyl | 6-methyl-3-methyl-imidazo[4,5-b]pyridine | 235-236 |
| 8 | CH, C—CF$_3$, CH, N | 3-F-phenyl | 6-methyl-2,3-dimethyl-imidazo[4,5-b]pyridine | 274-275 |
| 9 | CH, C—F, CH, CH | 3-F-phenyl | 7-methyl-2,3-dihydro-pyrido[3,2-b][1,4]oxazine | 265-266 |
| 10 | CH, C—F, CH, CH | 3-F-phenyl | 7-methyl-4-methyl-2,3-dihydro-pyrido[3,2-b][1,4]oxazine | 214-215 |
| 11 | CH, C—F, CH, CH | 3-F-phenyl | 6-methyl-2-methyl-3H-imidazo[4,5-b]pyridine | 299-300 |
| 12 | CH, C—F, CH, CH | 3-F-phenyl | 6-methyl-1-methyl-2-oxo-pyrido[3,2-b][1,4]oxazine | 248-250 |

TABLE 1-continued (I)

| No. | X$_1$, X$_2$, X$_3$, X$_4$ | Y | A | m.p. (° C.) |
|---|---|---|---|---|
| 13 | CH, C—F, CH, CH | 3-F-phenyl | 6-methyl-thiazolo[5,4-b]pyridin-2-yl-CH$_2$—O—C(O)—tBu | 224-225 |
| 14 | CH, C—F, CH, CH | 3-F-phenyl | 7-methyl-2,3-dihydro-[1,4]dioxino[2,3-b]pyridin-6-yl | 224-225 |
| 15 | CH, C—F, CH, CH | 3-F-phenyl | 7-hydroxy-5,6,7,8-tetrahydroquinolin-3-yl | 204-206 |
| 16 | CH, C—CF$_3$, CH, CH | 3-Me-phenyl | 6-methyl-2-(hydroxymethyl)-thiazolo[5,4-b]pyridin-2-yl | 315-316 |
| 17 | CH, CH, C—CF$_3$, CH | 3-Me-phenyl | 6-methyl-2-(hydroxymethyl)-thiazolo[5,4-b]pyridin-2-yl | 221-222 |
| 18 | CH, C—SiMe$_3$, CH, CH | 3-Me-phenyl | 6-methyl-2-(hydroxymethyl)-thiazolo[5,4-b]pyridin-2-yl | 154-155 |
| 19 | CH, CH, C—F, CH | 3-Me-phenyl | 6-methyl-2-(hydroxymethyl)-thiazolo[5,4-b]pyridin-2-yl | 257-258 |
| 20 | CH, C—CF$_3$, CH, CH | thiazol-2-yl | 6-methyl-2-(hydroxymethyl)-thiazolo[5,4-b]pyridin-2-yl | 282-283 |
| 21 | CH, CH, C—CF$_3$, CH | thiazol-2-yl | 6-methyl-2-(hydroxymethyl)-thiazolo[5,4-b]pyridin-2-yl | 243-244 |
| 22 | CH, C—SiMe$_3$, CH, CH | thiazol-2-yl | 6-methyl-2-(hydroxymethyl)-thiazolo[5,4-b]pyridin-2-yl | 270-271 |
| 23 | CH, CH, C—F, CH | thiazol-2-yl | 6-methyl-2-(hydroxymethyl)-thiazolo[5,4-b]pyridin-2-yl | 151-153 |

TABLE 1-continued (I)

| No. | X₁, X₂, X₃, X₄ | Y | A | m.p. (° C.) |
|---|---|---|---|---|
| 24 | CH, C—CF₃, CH, N | 2-methylthiazole | 6-methyl-thiazolo[5,4-b]pyridine-2-methanol | 207-208 |
| 25 | CH, CH, C—SiMe₃, CH | 2-methylthiazole | 6-methyl-thiazolo[5,4-b]pyridine-2-methanol | 219-220 |
| 26 | CH, C—CF₃, CH, CH | 4-methylpyridine | 6-methyl-thiazolo[5,4-b]pyridine-2-methanol | 237-238 |
| 27 | CH, CH, C—CF₃, CH | 4-methylpyridine | 6-methyl-thiazolo[5,4-b]pyridine-2-methanol | 261-263 |
| 28 | CH, C—SiMe₃, CH, CH | 4-methylpyridine | 6-methyl-thiazolo[5,4-b]pyridine-2-methanol | 208-210 |
| 29 | CH, CH, C—F, CH | 4-methylpyridine | 6-methyl-thiazolo[5,4-b]pyridine-2-methanol | 290-291 |
| 30 | CH, C—CF₃, CH, N | 4-methylpyridine | 6-methyl-thiazolo[5,4-b]pyridine-2-methanol | 275-276 |
| 31 | CH, CH, C—SiMe₃, CH | 4-methylpyridine | 6-methyl-thiazolo[5,4-b]pyridine-2-methanol | 213-214 |
| 32 | CH, C—SiMe₃, CH, CH | 3-(trifluoromethyl)phenyl | 6-methyl-thiazolo[5,4-b]pyridine-2-methanol | 152-153 |
| 33 | CH, CH, C—F, CH | 3-(trifluoromethyl)phenyl | 6-methyl-thiazolo[5,4-b]pyridine-2-methanol | 217-218 |
| 34 | CH, C—CF₃, CH, N | 3-(trifluoromethyl)phenyl | 6-methyl-thiazolo[5,4-b]pyridine-2-methanol | 312-314 |

TABLE 1-continued (I)

| No. | $X_1, X_2, X_3, X_4$ | Y | A | m.p. (° C.) |
|---|---|---|---|---|
| 35 | CH, CH, C—SiMe$_3$, CH | CF$_3$-phenyl | thiazolo[5,4-b]pyridin-2-yl-CH(OH)- | 180-181 |
| 36 | CH, C—CF$_3$, CH, N | Me-phenyl | thiazolo[5,4-b]pyridin-2-yl-CH(OH)- | 335-336 |
| 37 | CH, CH, C—SiMe$_3$, CH | Me-phenyl | thiazolo[5,4-b]pyridin-2-yl-CH(OH)- | 168-169 |
| 38 | CH, C—CF$_3$, CH, CH | CF$_3$-phenyl | thiazolo[5,4-b]pyridin-2-yl-CH(OH)- | 237-239 |
| 39 | CH, CH, C—CF$_3$, CH | CF$_3$-phenyl | thiazolo[5,4-b]pyridin-2-yl-CH(OH)- | 197-198 |

The compounds according to the invention underwent in vitro and in vivo pharmacological tests that demonstrated their value as therapeutically active substances. These compounds have antagonist or agonist activity towards the TRPV1 (or VR1) receptors.

Test of Inhibition of the Current Induced with Capsaicin on Rat DRGs

Primary culture of rat dorsal root ganglion (DRG) cells:
DRG neurones naturally express the TRPV1 receptor.

The primary cultures of newborn rat DRGs are prepared using 1-day-old rats. Briefly, after dissection, the ganglions are trypsinized and the cells dissociated by mechanical trituration. The cells are resuspended in an Eagle basal culture medium containing 10% foetal calf serum, 25 mM KCl, 2 mM glutamine, 100 µg/ml gentamicin and 50 ng/ml of NGF, and then deposited on glass slides coated with laminin (0.25× $10^6$ cells per slide), which are then placed in Corning 12-well dishes. The cells are incubated at 37° C. in a humidified atmosphere containing 5% CO$_2$ and 95% air. Cytosine β-D-arabinoside (1 µM) is added 48 hours after culturing, to prevent the growth of non-neuronal cells. The slides are transferred into experimental chambers for the patch-clamp studies after 7-10 days of culturing.

Electrophysiology:

The measuring chambers (volume 800 µl) containing the cell preparation are placed on the platform of an inverted microscope (Olympus IMT2) equipped with Hoffman optics (Modulation Contrast, New York) and observed at a magnification of 400×. The chambers are continuously gravity-influxed (2.5 ml/min) using a solution distributor accepting 8 inlets and whose sole outlet, consisting of a polyethylene tube (aperture 500 µm), is placed less than 3 mm from the cell under study. The "whole cell" configuration of the patch-clamp technique was used. The borosilicate-glass pipettes (resistance 5-10 MOhms) are brought to the cell by means of a 3D piezoelectric micromanipulator (Burleigh, PC1000). The overall currents (membrane potential set at −60 mV) are recorded with an Axopatch 1D amplifier (Axon Instruments, Foster City, Calif.), connected to a PC running the Pclamp8 software (Axon Instrument). The current plots are recorded on paper and simultaneously digitized (sampling frequency 15 to 25 Hz) and acquired on the hard drive of the PC.

The application of a 300 nM capsaicin solution induces on the DRG cells (voltage set at −70 mV) an entering cationic current. In order to minimize the desensitization of the receptors, a minimum interval of 1 minute between two applications of capsaicin is observed. After a control period (stabilization of the capsaicin response alone), the test compounds are applied alone at a given concentration (concentration of 10 nM or 1 nM) for a time of 4 to 5 minutes, during which several capsaicin+compound tests are performed (to obtain the maximum inhibition). The results are expressed as a percentage of inhibition of the control capsaicin response.

In the case of the VR1 antagonist compounds, the percentages of inhibition of the capsaicin response (1 µM) are between 20% and 100% for the most active compounds of the invention tested at concentrations of from 0.1 to 10 nM. They are therefore effective antagonists of receptors of TRPV1 type. Table 2 gives an example of the percentage of inhibition obtained with the compounds of the invention.

TABLE 2

| Compound No. | % inhibition in DRG patch |
|---|---|
| 4 | 65.5% (0.1 nM) |
| 11 | 62% (100 nM) |

Pain Induced by Intraplantar Administration of Capsaicin to Mice.

The intraplantar injection of capsaicin to mice rapidly produces short-lived nociceptive behaviour, which is reflected by licking, biting and flexing of the administered leg. These nociceptive responses are probably associated with the activation of the local TRPV1 receptors by the capsaicin.

Methodology:

(E)-Capsaicin is initially diluted to 3 mg/ml in DMSO, and then diluted again for its final use to 1.5 μg/20 μl in physiological saline. The administration of solvent has no effect on the behaviour of the mouse. The capsaicin is injected into the hind legs of the animal, on the upper face.

The test compounds are administered orally 120 minutes before the injection of capsaicin. Two hours after administration of the compounds, the mice are placed in a glass beaker. The nociceptive behaviour of the animals is then assessed immediately by the experimenter, and the duration of the capsaicin-induced behavioural manifestations is timed over a period of 2 minutes (licking and biting, total or partial flexure of the injected leg).

For each compound, an inhibition corresponding to the mean of the capsaicin-induced nociceptive responses, in response to a dose of test product (expressed in mg/kg) administered orally to a sample of a given number (n) of mice, is determined.

Table 3 gives an example of a percentage of inhibition obtained with the compounds of the invention.

TABLE 3

| Compound No. | Dose | n | % inhibition of the capsaicin-induced nociceptive responses |
|---|---|---|---|
| 4 | 10 mg/kg | 10 | 37% (±8%) |

The compounds of the invention may thus be used for the preparation of medicaments, especially for the preparation of a medicament for preventing or treating pathologies in which receptors of TRPV1 type are involved.

The compounds of the invention may be useful for preventing or treating pathologies in which receptors of TRPV1 type are involved.

Thus, a subject of the invention is medicaments comprising at least one compound of formula (I), or a pharmaceutically acceptable salt, or alternatively a hydrate or a solvate of the said compound.

These medicaments find their therapeutic use especially in the prevention and/or treatment of pain and inflammation, chronic pain, neuropathic pain (trauma-related, diabetic, metabolic, infection-related or toxic pain, or pain induced by an anticancer or iatrogenic treatment), (osteo)arthritic pain, rheumatic pain, fibromyalgia, back pain, cancer-related pain, facial neuralgia, headaches, migraine, dental pain, burns, sunburn, animal bites or insect bites, post-herpetic neuralgia, muscular pain, trapped nerves (central and/or peripheral), spinal column and/or brain trauma, ischaemia (of the spinal column and/or the brain), neurodegeneration, haemorrhagic strokes (of the spinal column and/or of the brain) and post-stroke pain.

The compounds of the invention may also be used for preventing and/or treating metabolic disorders such as diabetes.

The compounds of the invention may be used for preventing and/or treating urological disorders such as hyperactivity of the bladder, vesical hyperreflexia, vesical instability, incontinence, urgent micturition, urinary incontinence, cystitis, nephritic colic, pelvic hypersensitivity and pelvic pain.

The compounds of the invention may be useful for preventing and/or treating gynaecological disorders, for instance vulvodynia and pain associated with salpingitis or with dysmenorrhoea.

These products may also be used for preventing and/or treating gastrointestinal disorders such as gastro-oesophageal reflux disorder, stomach ulcers, duodenal ulcers, functional dyspepsia, colitis, IBS, Crohn's disease, pancreatitis, oesophagitis and biliary colic.

Similarly, the products of the present invention may be useful in the prevention and/or treatment of respiratory disorders such as asthma, coughing, chronic obstructive pulmonary disease (COPD), bronchoconstriction and inflammatory disorders of the respiratory system.

These products may also be used for preventing and/or treating psoriasis, pruritus, dermal, ocular or mucous irritation, herpes and zona.

The compounds of the invention may also be used for treating depression.

The compounds of the invention may also be used for treating central nervous system diseases such as multiple sclerosis.

The compounds of the invention may also be used for treating cancers.

According to another of its aspects, the present invention relates to pharmaceutical compositions comprising, as active principle, at least one compound according to the invention. These pharmaceutical compositions contain an effective dose of at least one compound according to the invention or a pharmaceutically acceptable salt, a hydrate or a solvate of the said compound and also at least one pharmaceutically acceptable excipient.

The said excipients are chosen, according to the pharmaceutical form and the desired mode of administration, from the usual excipients known to those skilled in the art.

The pharmaceutical compositions of the present invention may be administered via the oral, sublingual, subcutaneous, intramuscular, intravenous, topical, local, intratracheal, intranasal, transdermal or rectal route. These compositions may be administered in a unit administration form, as a mixture with standard pharmaceutical excipients. They are intended to be administered to animals and human beings for the prophylaxis or treatment of the disorders or diseases mentioned above.

The appropriate unit forms of administration include oral forms such as tablets, soft or hard gel capsules, powders, granules and oral solutions or suspensions, sublingual, buccal, intratracheal, intraocular and intranasal administration forms, forms for administration by inhalation, topical, transdermal, subcutaneous, intramuscular or intravenous administration forms, rectal administration forms and implants. For topical application, the compounds according to the invention may be used in creams, gels, pomades or lotions.

By way of example, a unit form of administration of a compound according to the invention in tablet form may comprise the following components:

| | |
|---|---|
| Compound according to the invention | 50.0 mg |
| Mannitol | 223.75 mg |
| Croscarmellose sodium | 6.0 mg |
| Corn starch | 15.0 mg |
| Hydroxypropylmethylcellulose | 2.25 mg |
| Magnesium stearate | 3.0 mg |

The said unit forms are dosed to allow a daily administration of from 0.001 to 30 mg of active principle per kg of body weight, according to the galenical form.

There may be particular cases in which higher or lower dosages are appropriate: such dosages do not depart from the scope of the invention. According to the usual practice, the dosage that is appropriate for each patient is determined by the doctor according to the mode of administration, the weight and the response of the said patient.

The compounds of the invention may also be used for the preparation of medicaments, especially for the preparation of a medicament for preventing or treating pathologies in which receptors of TRPV1 type are involved, as mentioned previously.

According to another of its aspects, the present invention also relates to a method for treating the pathologies indicated above, which comprises the administration to a patient of an effective dose of a compound according to the invention, or a pharmaceutically acceptable salt, or hydrate or solvate thereof.

What is claimed is:

1. A compound corresponding to formula (I):

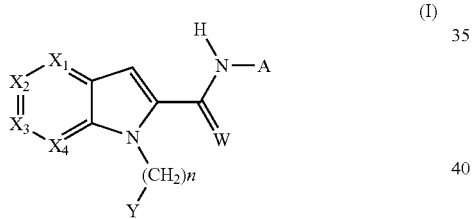

wherein:
$X_1$, $X_2$, $X_3$ and $X_4$ represent, independently of each other, a group C—$R_1$;
W represents an oxygen or sulfur atom;
n is equal to 0, 1, 2 or 3;
Y represents an aryl or a heteroaryl optionally substituted with one or more groups chosen from a halogen atom, a group $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, hydroxyl, $C_1$-$C_6$-alkoxy, $C_3$-$C_7$-cycloalkyloxy, $C_3$-$C_7$-cycloalkyl-$C_1$-$C_6$-alkylene-O—, $C_1$-$C_6$-fluoroalkoxy, cyano, C(O)NR$_4$R$_5$, nitro, NR$_4$R$_5$, $C_1$-$C_6$-thioalkyl, thiol, —S(O)—$C_1$-$C_6$-alkyl, —S(O)$_2$—$C_1$-$C_6$-alkyl, SO$_2$NR$_4$R$_5$, NR$_6$C(O)R$_7$, NR$_6$SO$_2$R$_8$, C(O)NR$_4$R$_5$, OC(O)NR$_4$R$_5$, —Si—(C$_1$-C$_6$-alkyl)$_3$, —SF$_5$, aryl-$C_1$-$C_5$-alkylene or aryl, heteroaryl-$C_1$-$C_5$-alkylene or heteroaryl; the groups $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy, $C_3$-$C_7$-cycloalkyl-$C_1$-$C_6$-alkylene-O— being optionally substituted with a hydroxyl group, $C_1$-$C_6$-alkoxy or NR$_4$R$_5$, the aryl and heteroaryl groups being optionally substituted with one or more substituents R$_9$, which may be identical to or different from each other;

A represents the group of formula:

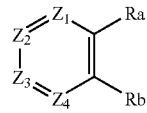

$Z_1$, $Z_2$, $Z_3$ and $Z_4$ represent, independently of each other, a nitrogen atom, a carbon atom or a group C—R$_2$,
at least one from among $Z_1$, $Z_2$, $Z_3$ and $Z_4$ corresponding to a nitrogen atom and
one from among $Z_1$, $Z_2$, $Z_3$ and $Z_4$, corresponding to a carbon atom, being bonded to the nitrogen atom of the amide or of the thioamide of formula (I);
Ra and Rb form, together with the carbon atoms that bear them,
either a partially unsaturated cycloalkyl, or an aryl;
or a heterocycle, or a heteroaryl, which is 5- to 7-membered, comprising from 1 to 3 heteroatoms chosen from O, S and N;
wherein when Ra and Rb together form, with the carbon atoms that bear them, a 5-membered ring, this ring comprising a nitrogen atom and carbon atoms, this ring being partially saturated or unsaturated, is excluded;
the partially unsaturated cycloalkyl, the aryl, the heterocycle or the heteroaryl are optionally substituted with one or more substituents R$_3$;
R$_1$ is chosen from a hydrogen atom, a halogen atom, $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryloxy-$C_1$-$C_6$-alkyl, heteroaryloxy-$C_1$-$C_6$-alkyl, aryl-$C_1$-$C_3$-alkylenoxy-$C_1$-$C_6$-alkyl, heteroaryl-$C_1$-$C_3$-alkylenoxy-$C_1$-$C_6$-alkyl, arylthio-$C_1$-$C_6$-alkyl, heteroarylthio-$C_1$-$C_6$-alkyl, aryl-$C_1$-$C_3$-alkylene-thio-$C_1$-$C_6$-alkyl, heteroaryl-$C_1$-$C_3$-alkylene-thio-$C_1$-$C_6$-alkyl, $C_1$-$C_6$-alkoxy, $C_3$-$C_7$-cycloalkyloxy, $C_3$-$C_7$-cycloalkyl-$C_1$-$C_3$-alkylenoxy, $C_1$-$C_6$-fluoroalkoxy, cyano, C(O)NR$_4$R$_5$, nitro, NR$_4$R$_5$, $C_1$-$C_6$-thioalkyl, $C_3$-$C_7$-cycloalkylthio, $C_3$-$C_7$-cycloalkyl-$C_1$-$C_3$-alkylene-thio, —S(O)—$C_1$-$C_6$-alkyl, —S(O)—$C_3$-$C_7$-cycloalkyl, —S(O)—$C_1$-$C_3$-alkylene-$C_3$-$C_7$-cycloalkyl, $C_1$-$C_6$-alkyl-S(O)$_2$—, $C_1$-$C_6$-fluoroalkyl-S(O)$_2$—, $C_3$-$C_7$-cycloalkyl-S(O)$_2$—, $C_3$-$C_7$-cycloalkyl-$C_1$-$C_3$-alkylene-S(O)$_2$—, SO$_2$NR$_4$R$_5$, —Si—(C$_1$-C$_6$-alkyl)$_3$, —SF$_5$, NR$_6$C(O)R$_7$, NR$_6$SO$_2$R$_8$, C(O)NR$_4$R$_5$, OC(O)NR$_4$R$_5$, aryl, heteroaryl, aryl-$C_1$-$C_5$-alkylene, heteroaryl-$C_1$-$C_5$-alkylene, aryloxy, arylthio, heteroaryloxy or heteroarylthio; the heteroaryl or aryl groups being optionally substituted with one or more substituents R$_9$, which may be identical to or different from each other;
R$_2$ represents a hydrogen atom, a halogen atom or a group $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy, $C_3$-$C_7$-cycloalkyl-$C_1$-$C_3$-alkylene-O—, hydroxyl, thiol or $C_1$-$C_6$-fluoroalkoxy;
R$_3$ represents, when it is borne by a carbon atom, a hydrogen atom or a hydroxyl, thiol, $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy, $C_3$-$C_7$-cycloalkyl-$C_1$-$C_3$-alkylenoxy, $C_1$-$C_6$-alkoxy-$C_1$-$C_3$-alkylene, $C_3$-$C_7$-cycloalkyloxy-$C_1$-$C_3$-alkylene, $C_3$-$C_7$-cycloalkyl-$C_1$-$C_3$-alkylenoxy-$C_1$-$C_3$-alkylene, C(O)NR$_4$R$_5$, C(O)O—$C_1$-$C_6$-alkyl, CO$_2$H, oxo or thio group; the groups $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy, $C_3$-$C_7$-cycloalkyl-$C_1$-$C_3$-alkylenoxy, $C_1$-$C_6$-alkoxy-$C_1$-$C_3$-alkylene, $C_3$-$C_7$-cycloalkyloxy-$C_1$-$C_3$-alkylene, $C_3$-$C_7$-cycloalkyl-$C_1$-$C_3$-alkylenoxy-$C_1$-$C_3$-alkylene are optionally substituted with a hydroxyl group, $C_1$-$C_6$-alkoxy, —OC(O)—$C_1$-$C_6$-alkyl or $NR_4R_5$;

or $R_3$ represents, when it is borne by a nitrogen atom, a hydrogen atom or a group $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl-C(O)—, $C_1$-$C_6$-alkyl-C(O)—, $C_3$-$C_7$-cycloalkyl-C(O)—, $C_3$-$C_7$-cycloalkyl-$C_1$-$C_3$-alkylene-C(O)—, $C_1$-$C_6$-fluoroalkyl-C(O)—, aryl-S(O), $C_1$-$C_6$-alkyl-S(O)—, $C_1$-$C_6$-fluoroalkyl-S(O)—, aryl-S(O)$_2$—, $C_1$-$C_6$-alkyl-S(O)$_2$—, $C_1$-$C_6$-fluoroalkyl-S(O)$_2$—, $C_3$-$C_7$-cycloalkyl-S(O)$_2$—, $C_3$-$C_7$-cycloalkyl-$C_1$-$C_3$-alkylene-S(O)$_2$—, $C_1$-$C_6$-alkyl-O—C(O)—, aryl-$C_1$-$C_3$-alkyl-O—C(O)—, $C_3$-$C_7$-cycloalkyl-O—C(O)—, $C_3$-$C_7$-cycloalkyl-$C_1$-$C_3$-alkylene-O—C(O)—, $C_1$-$C_6$-fluoroalkyl-O—C(O), aryl-O—C(O)—, heteroaryl-O—C(O)—, heteroaryl or aryl; the heteroaryl and aryl groups being optionally substituted with one or more substituents $R_9$, which may be identical to or different from each other; the groups $C_1$-$C_6$-alkyl, $C_3$-$C_7$-cycloalkyl, $C_3$-$C_7$-cycloalkyl-$C_1$-$C_3$-alkylene and $C_1$-$C_6$-fluoroalkyl are optionally substituted with a hydroxyl group, $C_1$-$C_6$-alkoxy or $NR_4R_5$;

$R_4$ and $R_5$, represent, independently of each other, a hydrogen atom or a group $C_1$-$C_6$-alkyl, $C_3$-$C_7$-cycloalkyl, $C_3$-$C_7$-cycloalkyl-$C_1$-$C_3$-alkylene, aryl-$C_1$-$C_5$-alkylene or aryl, or $R_4$ and $R_5$ together form, with the nitrogen atom that bears them, an azetidine, pyrrolidine, piperidine, azepine, morpholine, thiomorpholine, piperazine or homopiperazine group; the group $NR_4R_5$ being optionally substituted with a group $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene, aryl, heteroaryl, aryl-S(O)$_2$—, $C_1$-$C_6$-alkyl-S(O)$_2$—, $C_1$-$C_6$-fluoroalkyl-S(O)$_2$, $C_3$-$C_7$-cycloalkyl-S(O)$_2$—, $C_3$-$C_7$-cycloalkyl-$C_1$-$C_3$-alkylene-S(O)$_2$—, aryl-C(O)—, $C_1$-$C_6$-alkyl-C(O)—, $C_3$-$C_7$-cycloalkyl-C(O)—, $C_3$-$C_7$-cycloalkyl-$C_1$-$C_3$-alkylene-C(O)—, $C_1$-$C_6$-fluoroalkyl-C(O)—, hydroxyl, $C_1$-$C_6$-alkyloxy, $C_3$-$C_7$-cycloalkyloxy, $C_3$-$C_7$-cycloalkyl-$C_1$-$C_3$-alkylenoxy, $C_1$-$C_6$-fluoroalkyl, aryloxy-$C_1$-$C_6$-alkylene, aryloxy, heteroaryloxy-$C_1$-$C_6$-alkylene or heteroaryloxy;

$R_6$ and $R_7$ represent, independently of each other, a hydrogen atom or a group $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene or aryl; the aryl group being optionally substituted with one or more substituents chosen from a halogen atom and a group $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy, $C_3$-$C_7$-cycloalkyl-$C_1$-$C_3$-alkylenoxy, $C_1$-$C_6$-fluoroalkoxy, nitro or cyano;

or $R_6$ and $R_7$ together form a 4- to 7-membered lactam comprising the nitrogen atom and the C(O) group that bear them;

$R_8$ represents a group $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene or aryl; the aryl group being optionally substituted with one or more substituents chosen from a halogen atom, a group $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy, $C_3$-$C_7$-cycloalkyl-$C_1$-$C_3$-alkylenoxy, $C_1$-$C_6$-fluoroalkoxy, nitro or cyano;

or $R_6$ and $R_8$ together form a 4- to 7-membered sultam comprising the nitrogen atom and the $S(O)_2$ group that bear them;

$R_9$ represents a halogen atom, a group $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy, $C_3$-$C_7$-cycloalkyl-$C_1$-$C_3$-alkylenoxy, or $C_1$-$C_6$-fluoroalkoxy; these groups being optionally substituted with a group OH, $C_1$-$C_6$-alkoxy or $NR_4R_5$; or alternatively $R_9$ represents a nitro group, cyano or $NR_4R_5$;

the sulfur atom(s) of the compound of general formula (I) optionally being in oxidized form;

the nitrogen atom(s) of the compound of general formula (I) optionally being in oxidized form;

or an acid-addition salt thereof.

2. The compound of formula (I) according to claim 1, wherein:

$X_1$, $X_2$, $X_3$ and $X_4$ represent, independently of each other, a group C—$R_1$; and $R_1$ is as defined in formula (I) according to claim 1;

or an acid-addition salt thereof.

3. The compound of formula (I) according to claim 1, wherein:

$R_1$ is chosen from a hydrogen atom, a halogen atom and a group $C_1$-$C_6$-fluoroalkyl or —Si($C_1$-$C_6$-alkyl)$_3$;

or an acid-addition salt thereof.

4. The compound of formula (I) according to claim 1, wherein n is equal to 1;

or an acid-addition salt thereof.

5. The compound of formula (I) according to claim 1, wherein:

Y represents a phenyl, optionally substituted with one or more groups chosen from a halogen atom and a group $C_1$-$C_6$-alkyl or $C_1$-$C_6$-fluoroalkyl;

or an acid-addition salt thereof.

6. The compound of formula (I) according to claim 1, wherein:

W represents an oxygen atom;

or an acid-addition salt thereof.

7. The compound of formula (I) according to claim 1, wherein:

A represents the group of formula:

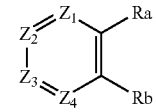

wherein A is chosen from the groups:

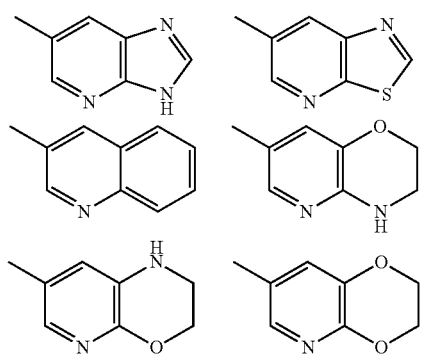

these groups being optionally substituted with $R_2$ and $R_3$ as defined in formula (I) of claim 1;

$R_2$ represents a hydrogen atom;

$R_3$ represents, when it is borne by a carbon atom, a hydrogen atom or a hydroxyl, $C_1$-$C_6$-alkyl or oxo group; the $C_1$-$C_6$-alkyl group is optionally substituted with a hydroxyl or —OC(O)—$C_1$-$C_6$-alkyl group;

or $R_3$ represents, when it is borne by a nitrogen atom, a hydrogen atom or a group $C_1$-$C_6$-alkyl;

or an acid-addition salt thereof.

8. The compound of formula (I) according to claim 1, wherein:

$X_1$, $X_2$, $X_3$ and $X_4$ represent, independently of each other, a group C—$R_1$;

$R_1$ is chosen from a hydrogen atom, a halogen atom and a group $C_1$-$C_6$-fluoroalkyl or —Si—($C_1$-$C_6$-alkyl)$_3$;

n is equal to 1;

Y represents an aryl or a heteroaryl optionally substituted with one or more groups chosen from a halogen atom and a group $C_1$-$C_6$-alkyl or $C_1$-$C_6$-fluoroalkyl;

W represents an oxygen atom;

A represents the group of formula:

wherein A is chosen from the groups:

these groups being optionally substituted with $R_2$ and $R_3$ as defined in formula (I) of claim 1;

$R_2$ represents a hydrogen atom;

$R_3$ represents, when it is borne by a carbon atom, a hydrogen atom or a hydroxyl, $C_1$-$C_6$-alkyl or oxo group; the $C_1$-$C_6$-alkyl group is optionally substituted with a hydroxyl or —OC(O)—$C_1$-$C_6$-alkyl group;

or $R_3$ represents, when it is borne by a nitrogen atom, a hydrogen atom or a group $C_1$-$C_6$-alkyl;

or an acid-addition salt thereof.

9. The compound of formula (I) according to claim 1, selected from the group consisting of:

N-(2,3-Dimethyl-3H-imidazo[4,5-b]pyrid-6-yl)-5-fluoro-1-[(3-fluorophenyl)methyl]-1H-indole-2-carboxamide;

N-(2-Methylthiazolo[5,4-b]pyrid-6-yl)-5-fluoro-1-[(3-fluorophenyl)methyl]-1H-indole-2-carboxamide;

N-(Thiazolo[5,4-b]pyrid-6-yl)-5-fluoro-1-[(3-fluorophenyl)methyl]-1H-indole-2-carboxamide;

N-(2-Hydroxymethylthiazolo[5,4-b]pyrid-6-yl)-5-fluoro-1-[(3-fluorophenyl)methyl]-1H-indole-2-carboxamide;

N-(Quinol-3-yl)-5-fluoro-1-[(3-fluorophenyl)methyl]-1H-indole-2-carboxamide;

N-(2-Hydroxymethyl-3-methyl-3H-imidazo[4,5-b]pyrid-6-yl)-5-fluoro-1-[(3-fluorophenyl)methyl]-1H-indole-2-carboxamide;

N-(3-Methyl-3H-imidazo[4,5-b]pyrid-6-yl)-5-fluoro-1-[(3-fluorophenyl)methyl]-1H-indole-2-carboxamide;

N-(3,4-Dihydro-2H-pyrido[3,2-b][1,4]oxazin-7-yl)-5-fluoro-1-[(3-fluorophenyl)methyl]-1H-indole-2-carboxamide;

N-(4-Methyl-3,4-dihydro-2H-pyrido[3,2-b][1,4]oxazin-7-yl)-5-fluoro-1-[(3-fluorophenyl)methyl]-1H-indole-2-carboxamide;

N-(2-Methyl-3H-imidazo[4,5-b]pyrid-6-yl)-5-fluoro-1-[(3-fluorophenyl)methyl]-1H-indole-2-carboxamide;

N-(1-Methyl-2-oxo-2,3-dihydro-1H-pyrido[2,3-b][1,4]oxazin-7-yl)-5-fluoro-1-[(3-fluoro-phenyl)methyl]-1H-indole-2-carboxamide;

[6-[[[5-Fluoro-1-[(3-fluorophenyl)methyl]-1H-indol-2-yl]carbonyl]amino]thiazolo[5,4-b]pyrid-2-yl]methyl 2,2-dimethylpropanoate;

N-(2,3-Dihydro-[1,4]dioxino[2,3-b]pyrid-7-yl))-5-fluoro-1-[(3-fluorophenyl)methyl]-1H-indole-2-carboxamide;

N-(6-Hydroxy-5,6,7,8-tetrahydroquinol-3-yl)-5-fluoro-1-[(3-fluorophenyl)methyl]-1H-indole-2-carboxamide;

N-(2-Hydroxymethylthiazolo[5,4-b]pyrid-6-yl)-5-trifluoromethyl-1-[(3-methylphenyl)-methyl]-1H-indole-2-carboxamide;

N-(2-Hydroxymethylthiazolo[5,4-b]pyrid-6-yl)-6-trifluoromethyl-1-[(3-methylphenyl)-methyl]-1H-indole-2-carboxamide;

N-(2-Hydroxymethylthiazolo[5,4-b]pyrid-6-yl)-5-trimethylsilyl-1-[(3-methylphenyl)-methyl]-1H-indole-2-carboxamide;

N-(2-Hydroxymethylthiazolo[5,4-b]pyrid-6-yl)-6-fluoro-1-[(3-methylphenyl)methyl]-1H-indole-2-carboxamide;

N-(2-Hydroxymethylthiazolo[5,4-b]pyrid-6-yl)-5-trifluoromethyl-1-[(thiazol-2-yl)methyl]-1H-indole-2-carboxamide;

N-(2-Hydroxymethylthiazolo[5,4-b]pyrid-6-yl)-6-trifluoromethyl-1-[(thiazol-2-yl)methyl]-1H-indole-2-carboxamide;

N-(2-Hydroxymethylthiazolo[5,4-b]pyrid-6-yl)-5-trimethylsilyl-1-[(thiazol-2-yl)methyl]-1H-indole-2-carboxamide;

N-(2-Hydroxymethylthiazolo[5,4-b]pyrid-6-yl)-6-fluoro-1-[(thiazol-2-yl)methyl]-1H-indole-2-carboxamide;

N-(2-Hydroxymethylthiazolo[5,4-b]pyrid-6-yl)-6-trimethylsilyl-1-[(thiazol-2-yl)methyl]-1H-indole-2-carboxamide;

N-(2-Hydroxymethylthiazolo[5,4-b]pyrid-6-yl)-5-trifluoromethyl-1-[(pyrid-4-yl)methyl]-1H-indole-2-carboxamide;
N-(2-Hydroxymethylthiazolo[5,4-b]pyrid-6-yl)-6-trifluoromethyl-1-[(pyrid-4-yl)methyl]-1H-indole-2-carboxamide;
N-(2-Hydroxymethylthiazolo[5,4-b]pyrid-6-yl)-5-trimethylsilyl-1-[(pyrid-4-yl)methyl]-1H-indole-2-carboxamide;
N-(2-Hydroxymethylthiazolo[5,4-b]pyrid-6-yl)-6-fluoro-1-[(pyrid-4-yl)methyl]-1H-indole-2-carboxamide;
N-(2-Hydroxymethylthiazolo[5,4-b]pyrid-6-yl)-6-trimethylsilyl-1-[(pyrid-4-yl)methyl]-1H-indole-2-carboxamide;
N-(2-Hydroxymethylthiazolo[5,4-b]pyrid-6-yl)-5-trimethylsilyl-1-[[(3-trifluoromethyl)-phenyl]methyl]-1H-indole-2-carboxamide;
N-(2-Hydroxymethylthiazolo[5,4-b]pyrid-6-yl)-6-fluoro-1-[[(3-trifluoromethyl)phenyl]-methyl]-1H-indole-2-carboxamide;
N-(2-Hydroxymethylthiazolo[5,4-b]pyrid-6-yl)-6-trimethylsilyl-1-[[(3-trifluoromethyl)-phenyl]methyl]-1H-indole-2-carboxamide;
N-(2-Hydroxymethylthiazolo[5,4-b]pyrid-6-yl)-6-trimethylsilyl-1-[(3-methylphenyl)-methyl]-1H-indole-2-carboxamide;
N-(2-Hydroxymethylthiazolo[5,4-b]pyrid-6-yl)-5-trifluoromethyl-1-[[(3-trifluoromethyl)-phenyl]methyl]-1H-indole-2-carboxamide; and
N-(2-Hydroxymethylthiazolo[5,4-b]pyrid-6-yl)-6-trifluoromethyl-1-[[(3-trifluoromethyl)-phenyl]methyl]-1H-indole-2-carboxamide;
or an acid-addition salt thereof.

10. A process for preparing a compound of formula (I) according to claim 1, comprising reacting a compound of formula (II):

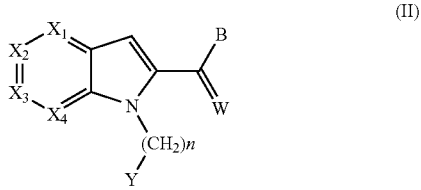

(II)

wherein $X_1$, $X_2$, $X_3$, $X_4$, n, Y and W are as defined in formula (I) according to claim 1;

with a compound of general formula (III),

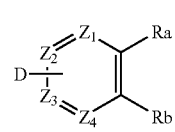

(III)

wherein $Z_1$, $Z_2$, $Z_3$, $Z_4$, Ra and Rb are as defined in formula (I) according to claim 1; and
  when B represents a hydroxyl group and D represents an amino group, in the presence of a coupling agent in a solvent;
  when B represents a chlorine atom and D represents an amino group, by reaction in solution in a solvent;
  when B represents a group $C_1$-$C_6$-alkoxyl, $C_3$-$C_7$-cycloalkyloxy, $C_3$-$C_7$-cycloalkyl-$C_1$-$C_3$-alkylenoxy- or aryl-$C_1$-$C_3$-alkylenoxy and D represents an amino group, by transformation of the compound of formula (III) into an amide via the prior action of trimethylaluminium on the amines of general formula (III), and then by reacting the amide obtained with the compound of formula (II) in a refluxing solvent; or
  when B represents an $NH_2$ group, W represents an oxygen atom and D corresponds to a leaving group, in the presence of a copper salt in catalytic amount, a catalytic amount of a copper ligand, and a base, in a solvent.

11. A pharmaceutical composition comprising a compound of formula (I) according to claim 1, or a pharmaceutically acceptable salt of said compound, in combination with at least one pharmaceutically acceptable excipient.

12. A pharmaceutical composition comprising a compound of formula (I) according to claim 2, or a pharmaceutically acceptable salt of said compound, in combination with at least one pharmaceutically acceptable excipient.

13. A pharmaceutical composition comprising a compound of formula (I) according to claim 3, or a pharmaceutically acceptable salt of said compound, in combination with at least one pharmaceutically acceptable excipient.

14. A pharmaceutical composition comprising a compound of formula (I) according to claim 9, or a pharmaceutically acceptable salt of said compound, in combination with at least one pharmaceutically acceptable excipient.

* * * * *